United States Patent
Song

(10) Patent No.: US 11,685,895 B2
(45) Date of Patent: Jun. 27, 2023

(54) METHOD FOR MANUFACTURING MICROALGAE MICRO POWDER CONTAINING ASTAXANTHIN AND FATTY ACIDS WITH ENHANCED PENETRATION PERFORMANCE AND FOOD AVAILABILITY

(71) Applicant: Sung Eun Song, Boeun-gun (KR)

(72) Inventor: Sung Eun Song, Boeun-gun (KR)

(73) Assignee: Sung Eun Song, Chungcheongbuk-do (KR)

( * ) Notice: Subject to any disclaimer, the term of this patent is extended or adjusted under 35 U.S.C. 154(b) by 279 days.

(21) Appl. No.: 17/120,119

(22) Filed: Dec. 12, 2020

(65) Prior Publication Data

US 2021/0189324 A1    Jun. 24, 2021

(30) Foreign Application Priority Data

Dec. 18, 2019  (KR) .......................... 10-2019-0169836

(51) Int. Cl.
*C12N 1/12*    (2006.01)
*A23L 17/60*   (2016.01)
*A23L 33/115*  (2016.01)

(52) U.S. Cl.
CPC ................ *C12N 1/12* (2013.01); *A23L 17/60* (2016.08); *A23L 33/115* (2016.08)

(58) Field of Classification Search
CPC ....................................................... C12N 1/12
See application file for complete search history.

(56) References Cited

FOREIGN PATENT DOCUMENTS

| KR | 10-2016-0008921 | 1/2016 | |
|----|-----------------|--------|--|
| KR | 10-2017-0096218 | 8/2017 | |
| WO | WO-2004043139 A2 * | 5/2004 | ............. A23K 10/16 |

OTHER PUBLICATIONS

John A.Bon et al.;Isolation of astaxanthin-overproducing mutansts of Phaffia rhodozyma; Biotechnology Letters, vol. 19, No. 2, Feb. 1997, pp. 109-112, Department of Biological Sciences, Illinois State University,IL, USA.

* cited by examiner

*Primary Examiner* — Rosanne Kosson

(57) ABSTRACT

The present invention relates to a method for manufacturing microalgae micro powder containing astaxanthin and fatty acids with enhanced penetration performance and food availability, and more particularly, to a method for manufacturing microalgae micro powder containing astaxanthin and fatty acids with enhanced penetration performance and food availability, in which four kinds of functional microalgae are selected and mass-cultured so as to be processed into a dietary shape for easy penetration performance.

9 Claims, 15 Drawing Sheets

(a)

(b)

(a)

(b)

(a)

(b)

(c)

(d)

(a)

(b)

(c)

(d)

(a)

(b)

(c)

(d)

(a)

(b)

(c)

METHOD FOR MANUFACTURING MICROALGAE MICRO POWDER CONTAINING ASTAXANTHIN AND FATTY ACIDS WITH ENHANCED PENETRATION PERFORMANCE AND FOOD AVAILABILITY

BACKGROUND OF THE INVENTION

1. Field of the Invention

The present invention relates to a method for manufacturing microalgae micro powder containing astaxanthin and fatty acids with enhanced penetration performance and food availability, and more particularly, to a method for manufacturing microalgae micro powder containing astaxanthin and fatty acids with enhanced penetration performance and food availability, in which four kinds of functional microalgae are selected and mass-cultured so as to be processed into a dietary shape for easy penetration performance.

2. Description of the Related Art

A commercial production of astaxanthin has been mainly dependent on chemical synthesis until now (Non-Patent Document 1). However, production methods by microorganisms are gradually gaining popularity due to legal regulations and consumer desire for natural products. The biosynthesis of astaxanthin is found only in microorganisms. *Haematococcus pluvialis* as microalgae (Johnson E A Int. Microbiol. 6, 169-174 (2003)) and *Phaffia rhodozyma* as yeast (Bhosale P and Bernstein P S, Microbial xanthophylls. Appl. Microbiol. Biotechnol. 68:445-455 (2005)), are known as microbial systems that can be industrially produced. However, the culture of microalgae such as *Haematococcus pluvialis* requires a long-term culture, has a serious pollution problem, and requires a highly expensive process. On the contrary, the yeast *Phaffia rhodozyma* is relatively easily fermented and has a low cost process, but difficultly digested and absorbed due to a hard cell wall. Since an astaxanthin content of a wild *Phaffia rhodozyma* strain is about 0.3 mg to about 5 mg per gram of dry cells, *Phaffia rhodozyma* needs a mutation to increase the astaxanthin content.

Meanwhile, *Dunaliella* is a eukaryote belonging to the green algae that performs photosynthesis, and has a high salt adaptation range to survive even at salt concentrations ranging from an equivalent to 1/10 of seawater to 5 M close to a saturated solution. In taxonomy, *Dunaliella* is classified as the family Dunaliellaceae of the order Volvocales belonging to the class Chlrophyceae of the division Chlorophyta, and is a single-celled green alga having a cell volume up to 50 mm² and to 100 mm². A cell thereof is surrounded by a thin mucous membrane having elasticity and does not have a rigid polysaccharide cell wall of an ordinary plant.

In general, microalgae of the genus *Dunaliella* are found in places with low nitrogen content, strong sunlight, and high salt concentration, and found to exhibit a yellow-green to orange color by accumulating beta-carotene in cells when exposed to the above intense environmental stress conditions. The beta-carotene has been reported as being accumulated together with oily granulocytes into a thylakoid intermembrane space in chloroplast. It is presumed that the accumulated beta-carotene is supposed to protect the photosynthetic system from strong light.

The algae of the genus *Dunaliella* may have the ability to produce at least one pigment selected from the group including lutein, zeaxanthin, chlorophyll b, chlorophyll a, and p-carotene. Since large amounts of zeaxanthin and lutein can be produced by using the algae of the genus *Dunaliella* with little energy, zeaxanthin and lutein may be efficiently manufactured and supplied at the industrial level. The composition of the present invention may be applied as a raw material for foods, health functional foods and medicines containing pigments of zeaxanthin and lutein. In addition, since seawater may be used as a culture medium in consideration of the physiological characteristics of *Dunaliella* as euryhaline microalgae, and the geographical characteristics of Korea having three sides of the sea, it is expected that costs can be reduced and related industries can be developed (Patent Document 1).

(Patent Document 1) KR10-1901608 B1

(Non-Patent Document 1) Ernst H, Recent advances in industrial carotenoid synthesis. Pure Appl. Chem. 74, 1369-1382 (2002)

SUMMARY OF THE INVENTION

The present invention provides a method for manufacturing microalgae micro powder containing astaxanthin and fatty acids with enhanced penetration performance and food availability, in which four kinds of functional microalgae are selected and mass-cultured so as to be processed into a dietary form for easy penetration performance.

In order to solve the above problem, the present invention provides a method for manufacturing microalgae micro powder containing astaxanthin and fatty acids with enhanced penetration performance and food availability, which includes: a microalgae culturing step of mass-culturing four microalgal strains of *Phaffia rhodozyma*, *Dunaliella salina*, *Chlorella vulgaris*, and *Spirulina platensis* in a medium; a microalgae collecting step of separating and collecting the cultured microalgae from the medium; an oil extracting step of extracting an oil ingredient by compressing the microalgae; a powder processing step of pulverizing the oil extracted microalgae; and a powder mixing step of mixing the four microalgae powders of *Phaffia rhodozyma*, *Dunaliella salina*, *Chlorella vulgaris*, and *Spirulina platensis* that have been subjected to the powder processing step, wherein the microalgae culturing step, the microalgae collecting step, the oil extracting step, and the powder processing step are performed for each of the four microalgae of *Phaffia rhodozyma*, *Dunaliella salina*, *Chlorella vulgaris*, and *Spirulina platensis*.

According to the present invention, in the powder mixing step, powder of *Phaffia rhodozyma*, *Dunaliella salina*, *Chlorella vulgaris*, and *Spirulina platensis* may be mixed with each other in the same ratio.

According to the present invention, the microalgae culturing step for *Phaffia rhodozyma* may include: a mutation promoting step of inducing a mutation by applying stress to *Phaffia rhodozyma* cells; a mutant selecting step of selecting and separating a strain highly containing astaxanthin from the mutated *Phaffia rhodozyma* cells; a medium composing step of composing a liquid medium for culturing *Phaffia rhodozyma*; and a mass-culturing step of culturing the selected *Phaffia rhodozyma* strain in the liquid medium.

According to the present invention, in the mutation promoting step, methylnitronitrosoguanidine (MNNG) may be added to *Phaffia rhodozyma* cells to induce the mutation.

According to the present invention, in the mutation promoting step, a mutation may be induced by performing the culture under a light condition with illuminance of 18,000 lx to 21,000 lx.

According to the present invention, the microalgae culturing step for *Dunaliella salina* may include: a mutation promoting step of inducing a mutation by applying stress to *Dunaliella salina* cells; a mutant selecting step of selecting and separating a strain highly containing beta-carotene from the mutated *Dunaliella salina* cells; a medium composing step of composing a liquid medium for culturing *Dunaliella salina*; and a mass-culturing step of culturing the selected *Dunaliella salina* strain in the liquid medium, wherein, in the mutation promoting step, a mutation may be induced by performing the culture under a light condition with illuminance of 18,000 lx to 21,000 lx.

According to the present invention, in the microalgae culturing step, microalgae may be mass-cultured in a medium containing at least one of ionized calcium and silicic acid.

According to the present invention, in the microalgae collecting step, an aqueous ionized calcium solution having a content of 70 mg/L or more of calcium may be administered to culture water in which microalgae is cultured, and microalgae floating on the surface may be collected.

According to one embodiment of the present invention, four kinds of functional microalgae of *Phaffia rhodozyma*, *Dunaliella salina*, *Chlorella vulgaris*, and *Spirulina platensis* can be mass-produced so as to be processed into a dietary form for easy penetration performance.

According to one embodiment of the present invention, the culture efficiency, collection efficiency and dietary availability of the microalgae can be increased.

According to one embodiment of the present invention, the microalgae micro powder can be prepared with increased content of useful ingredients by inducing the mutation of microalgae.

DETAILED DESCRIPTION OF THE INVENTION

Figure 1:
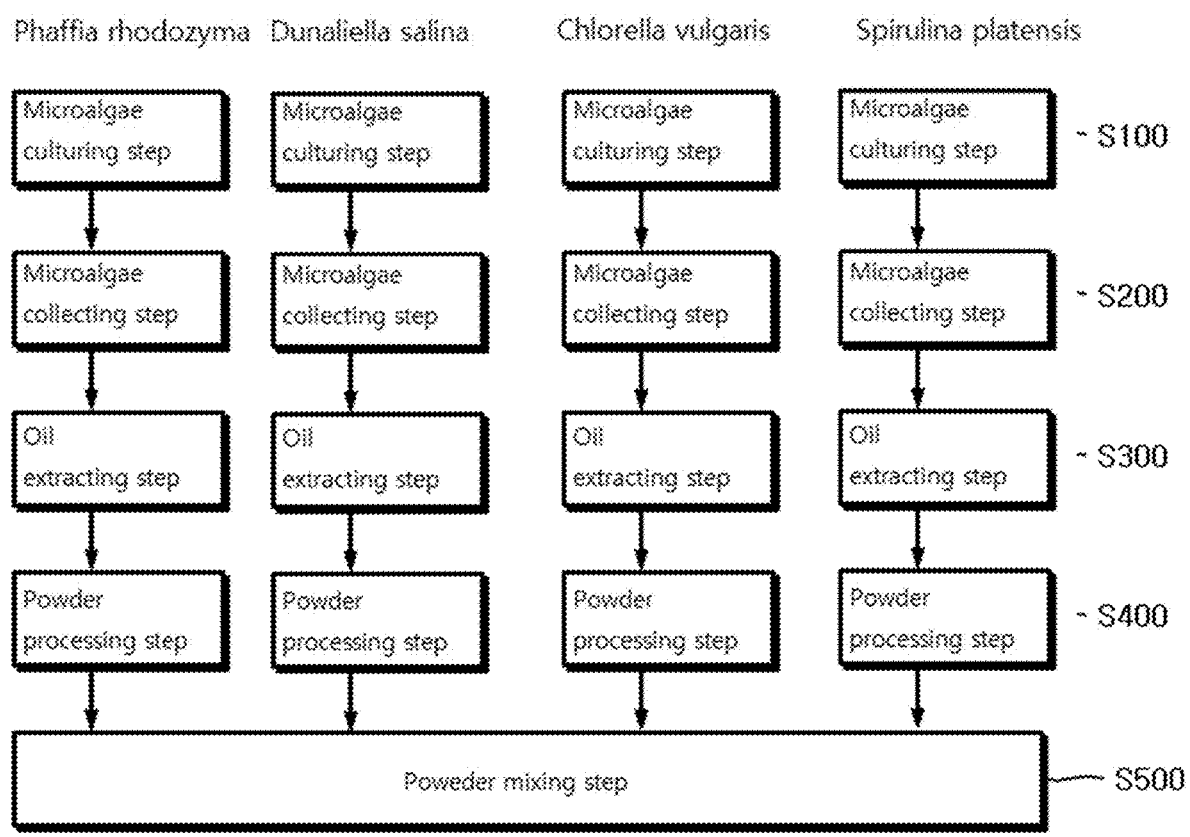
FIG. 1 is a diagram schematically showing a method for preparing microalgae micro powder according to one embodiment of the present invention.

Hereinafter, various embodiments and/or aspects will be described with reference to the drawings. In the following description, numerous specific details are set forth in order to provide a thorough understanding of one or more aspects for the purpose of explanation. However, it shall also be appreciated by those having ordinary skill in the art that such aspect(s) may be carried out without the specific details. The following description and accompanying drawings will be set forth in detail for specific illustrative aspects among one or more aspects. However, the aspects are merely illustrative and some of various ways among principles of the various aspects may be employed, and the descriptions set forth herein are intended to include all the various aspects and equivalents thereof.

The terms "embodiment", "example", "aspect" or the like used herein may not be construed in that an aspect or design set forth herein is preferable or advantageous than other aspects or designs.

Further, the term "or" is intended to signify an inclusive "or" rather than an exclusive "or". In other words, unless otherwise specified or contextually unclear, the expression "X uses A or B" is intended to signify one of natural inclusive substitutions. In other words, when X uses A, X uses B, or X uses both A and B, the expression "X uses A or B" may apply to either of the above cases. In addition, it is apparent to be understood that the term "and/or" as used herein refers to and includes all possible combinations of one or more among related items listed.

In addition, the terms "include" and/or "comprise" specify the presence of the corresponding feature and/or element, but do not preclude the possibility of the presence or addition of one or more other features, elements or combinations thereof.

In addition, in the present specification, it will be understood that singular expressions such as "one" include plural expressions unless clearly indicate otherwise.

In addition, the terms including an ordinal number such as first and second may be used to describe various elements, however, the elements are not limited by the terms. The terms are used only for the purpose of distinguishing one element from another element. For example, the first element may be referred to as the second element without departing from the scope of the present invention, and similarly, the second element may also be referred to as the first element. The term "and/or" includes any one of a plurality of related listed items or a combination thereof.

In addition, the term used herein is merely for the purpose of illustrating a particular embodiment, and it is not intended to limit the present invention. The singular expression includes a plural expression unless the context clearly means otherwise. In the specification herein, it should be understood that the term such as "include" and "have" is intended to designate the presence of feature, number, step, operation, element, component, or a combination thereof recited in the specification, which does not preclude the possibility of the presence or addition of one or more other features, numbers, steps, operations, elements, components, or combinations thereof.

In addition, in the embodiments of the present invention, unless defined otherwise, all terms used herein including technical or scientific terms have the same meaning as commonly understood by those having ordinary skill in the art. Terms such as those defined in generally used dictionaries should be interpreted to have the meaning consistent with the meaning in the context of the related art, should not be interpreted as an ideal or excessively formal meaning unless expressly defined in one embodiment of the present invention.

Preparation of Microalgae Micro Powder

FIG. 1 is a diagram schematically showing a method for preparing microalgae micro powder according to one embodiment of the present invention.

Referring to FIG. 1, the method for manufacturing microalgae micro powder containing astaxanthin and fatty acids with enhanced penetration performance and food availability according to one embodiment of the present invention includes: a microalgae culturing step S100 of mass-culturing four microalgal strains of *Phaffia rhodozyma, Dunaliella salina, Chlorella vulgaris,* and *Spirulina platensis* in a medium; a microalgae collecting step S200 of separating and collecting the cultured microalgae from the medium; an oil extracting step S300 of extracting an oil ingredient by compressing the microalgae; a powder processing step S400 of pulverizing the oil extracted microalgae; and a powder mixing step S500 of mixing the four microalgae powders of *Phaffia rhodozyma, Dunaliella salina, Chlorella vulgaris,* and *Spirulina platensis* that have been subjected to the powder processing step S400.

Referring to FIG. 1, according to one embodiment of the present invention, the microalgae culturing step S100, the microalgae collecting step S200, the oil extracting step S300, and the powder processing step S400 may be performed for each of the four microalgae of *Phaffia rhodozyma, Dunaliella salina, Chlorella vulgaris,* and *Spirulina platensis*. In other words, the microalgae culturing step S100, the microalgae collecting step S200, the oil extracting step S300, and the powder processing step S400 are performed with respect to each microalgae of *Phaffia rhodozyma, Dunaliella salina, Chlorella vulgaris,* and *Spirulina platensis*, and the microalgae powders generated through the powder processing steps S400 are mixed through the powder mixing step S500.

In the powder mixing step S500 according to one embodiment of the present invention, powders of *Phaffia rhodozyma, Dunaliella salina, Chlorella vulgaris,* and *Spirulina platensis* may be mixed in the same ratio to each other.

Figure 2:
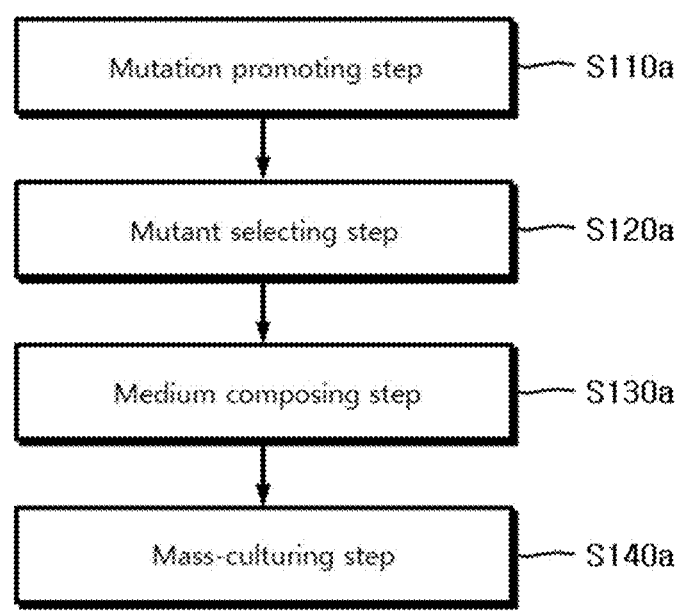
FIG. 2 is a diagram schematically showing detailed steps of a microalgae culturing step of *Phaffia rhodozyma* according to one embodiment of the present invention.

FIG. 2 is a diagram schematically showing detailed steps of a microalgae culturing step of *Phaffia rhodozyma* according to one embodiment of the present invention.

Referring to FIG. 2, the microalgae culturing step S100 for *Phaffia rhodozyma* according to one embodiment of the present invention may include: a mutation promoting step S110a of causing a mutation by applying stress to *Phaffia rhodozyma* cells; a mutant selecting step S120a of selecting and separating a strain highly containing astaxanthin from the mutated *Phaffia rhodozyma* cells; a medium composing step S130a of composing a liquid medium for culturing *Phaffia rhodozyma*; and a mass-culturing step S140a of culturing the selected *Phaffia rhodozyma* strain in the liquid medium.

The detailed steps of the microalgae culturing step S100 are processes for mass production by increasing the content of astaxanthin produced by the *Phaffia rhodozyma*. According to the present invention, a mutation of the *Phaffia rhodozyma* is induced to mass-produce astaxanthin, and a strain mass-producing astaxanthin is selected and cultured.

According to one embodiment of the present invention, in the mutation promoting step S110a, stress is applied to *Phaffia rhodozyma* cells to cause the mutation. Excellent individuals survived from the above stress are selected through the mutation selecting step S120a, so that large amounts of astaxanthin may be produced from *Phaffia rhodozyma*.

In the mutation promoting step S110a according to one embodiment of the present invention, methylnitronitrosoguanidine (MNNG) may be added to *Phaffia rhodozyma* cells to induce the mutation. Methylnitronitrosoguanidine, also known as MNNG or NTG, may cause a mutation of *Phaffia rhodozyma*. MNNG may be mixed with a liquid medium after dissolved into acetone. According to one embodiment of the present invention, acetone formed by dissolving MNNG therein and distilled water may be diluted in the weight ratio of 1:8 to 1:10, so that a solution to be added to the liquid medium may be generated.

Since a dead rate of microalgae may vary according to a concentration, a processing temperature, and a processing time of MNNG, and the probability of obtaining a mutant may vary according to the dead rate, these conditions are required to be appropriately adjusted. Preferably, the dead rate may be adjusted to be 95% to 98%.

According to one embodiment of the present invention, the MNNG solution is added at a concentration of 0.1 mg/ml, suspension-cultured for 20 minutes, washed once with sterile water and once with a phosphate buffer solution (pH 7.0), suspended in a YM medium and cultured for 12 to 16 hours at 20° C., diluted with sterile water, and smeared.

Meanwhile, in the mutation promoting step S110a according to another embodiment of the present invention, a mutation may be induced by performing the culture under a light condition with illuminance of 18,000 lx to 21,000 lx. *Phaffia rhodozyma* subjected to the above light stress may be mutated. More preferably, the mutation may be induced by performing the culture under a light condition with illuminance of 19,000 lx to 20,000 lx.

In the mutant selecting step S120a according to one embodiment of the present invention, the *Phaffia rhodozyma* mutated in the mutation promoting step 110a is cultured, and a strain highly containing astaxanthin is selected. According to one embodiment of the present invention, since astaxanthin is a reddish pigment, a strain having a color more reddish than a parent strain may be selected to select *Phaffia rhodozyma* having a high astaxanthin content, that is, smoothly producing astaxanthin.

In the medium composing step S130a, a liquid medium for culturing the *Phaffia rhodozyma* is composed. According to one embodiment of the present invention, the liquid medium may include 10 g of glucose, 9.6 g of CSL, 3 g of yeast extract, 5 g of peptone, 0.6 g of monobasic potassium phosphate, 0.5 g of magnesium sulfate, 0.25 g of copper sulfate, 0.15 g of calcium chloride, 0.03 g of zinc sulfate, 0.02 g of thiamine, and 0.0001 g of biotin, within 10% of an error range per liter.

Meanwhile, according to one embodiment of the present invention, the liquid medium may further include at least one of ionized calcium and silicic acid in the above-described liquid medium. Accordingly, *Phaffia rhodozyma* may exhibit a higher culture rate in the liquid medium further including ionized calcium and silicic acid.

In the mass-culturing step S140a, the mutant selected in the mutant selecting step S120a may be cultured in the liquid medium composed in the medium composing step S130a. In the mass-culturing step S140a according to one embodiment of the present invention, the culture may be performed under a condition maintaining a stirring speed of 250 rpm to 350 rpm, a culture temperature of 18 to 22° C., and a pH of 4.8 to 5.2.

In addition, according to one embodiment of the present invention, gas obtained by mixing air with oxygen at the ratio of 9:1 to 11:1 may be supplied into a fermentation tank for culturing the *Phaffia rhodozyma* at a rate of 4 vvm to 6 vvm.

Meanwhile, according to one embodiment of the present invention, the culture may be performed under light conditions of 4,000 lx to 8,000 lx, more preferably 5,500 lx to 6,500 lx.

Figure 3:
FIG. 3 is a diagram schematically showing a mutant selection process of *Phaffia rhodozyma* according to one embodiment of the present invention.
Figure 3:
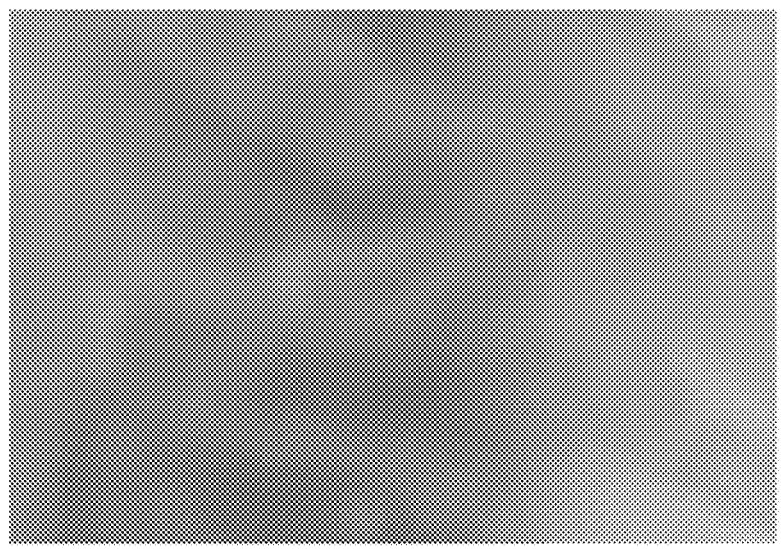

FIG. 3 is a diagram schematically showing a mutant selection process of *Phaffia rhodozyma* according to one embodiment of the present invention.

FIG. 3(a) shows a mutant survived from stress through the mutation promoting step S110a. According to one embodiment of the present invention, a strain having a red color is selected and cultured among the *Phaffia rhodozyma* mutated through the mutant selecting step S120a.

FIG. 3(b) shows a state in which the mutant selected through the mutant selecting step S120a is mass-cultured through the mass-culturing step S140a. It can be seen that astaxanthin was produced in large quantities by culturing the red strains in large quantities.

Figure 4:
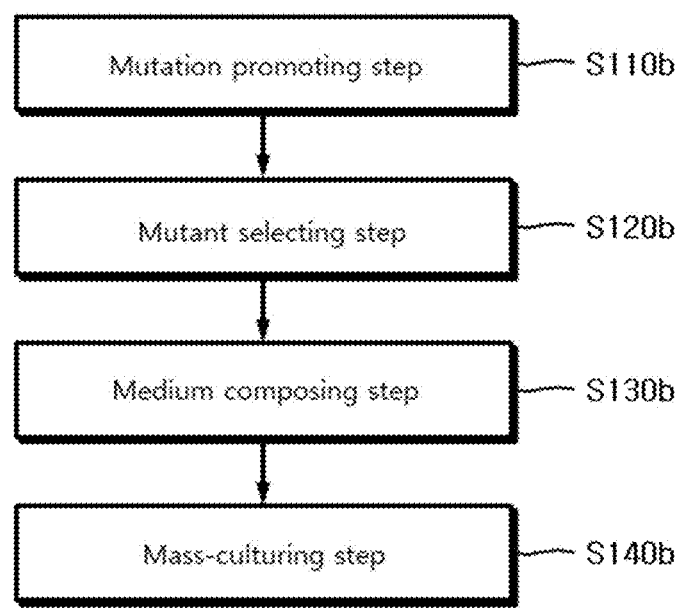
FIG. 4 is a diagram schematically showing detailed steps of a microalgae culturing step of *Dunaliella salina* according to one embodiment of the present invention.

FIG. 4 is a diagram schematically showing detailed steps of a microalgae culturing step of *Dunaliella salina* according to one embodiment of the present invention.

Referring to FIG. 4, the microalgae culturing step S100 for *Dunaliella salina* according to one embodiment of the present invention may include: a mutation promoting step S110b of causing a mutation by applying stress to *Dunaliella salina* cells; a mutant selecting step S120b of selecting and separating a strain highly containing beta-carotene from the mutated *Dunaliella salina* cells; a medium composing step S130c of composing a liquid medium for culturing *Dunaliella salina*; and a mass-culturing step S130d of culturing the selected *Dunaliella salina* strain in the liquid medium.

The detailed steps of the microalgae culturing step S100 as described above are processes for mass-production by increasing the content of beta-carotene produced by the *Dunaliella salina*. According to the present invention, the mutation of the *Dunaliella salina* may be induced to mass-produce beta-carotene, and a strain mass-producing beta-carotene may be selected and cultured.

In the mutation promoting step S110b according to one embodiment of the present invention, stress is applied to *Phaffia rhodozyma* cells to cause the mutation. Excellent individuals survived from the above stress are selected through the mutation selecting step S120b, so that large amounts of beta-carotene may be produced from *Dunaliella salina*.

In the mutation promoting step S110b according to one embodiment of the present invention, a mutation may be induced by performing the culture under a light condition with illuminance of 18,000 lx to 21,000 lx. *Dunaliella salina* subjected to the above light stress may be mutated. More preferably, the mutation may be induced by performing the culture under a light condition with illuminance of 19,000 lx to 20,000 lx.

In the mutant selecting step S120b according to one embodiment of the present invention, the *Dunaliella salina* mutated in the mutation promoting step 110b is cultured, and a strain highly containing beta-carotene is selected. According to one embodiment of the present invention, when the light stress is applied to cause the mutation, the *Dunaliella salina* survived from the light stress exhibits high beta-carotene productivity.

In the medium composing step S130b, a liquid medium for culturing the *Dunaliella salina* is composed. According to one embodiment of the present invention, the liquid medium may include 1 M of sodium chloride (NaCl), 5 mM of magnesium sulfate (MgSO4), 0.3 mM of calcium chloride (CaCl2)), 5 mM of potassium nitrate (KNO3), 0.2 mM of monobasic potassium phosphate (KH 2PO4), 50 mM of sodium hydrogen carbonate (NaHCO$_3$), 1.5 µM of ferrous chloride (FeCl3), 6 µM of EDTA, and 4.5 µM of cobalt chloride (CoCl2.6H2O), within 10% of an error range.

Meanwhile, according to one embodiment of the present invention, the liquid medium may further include at least one of ionized calcium and silicic acid in the above-described liquid medium. *Dunaliella salina* may exhibit a higher culture rate in the liquid medium further including ionized calcium and silicic acid.

In the mass-culturing step S140b, the mutant selected in the mutant selecting step S120b may be cultured in the liquid medium composed in the medium composing step S130b. In the mass-culturing step S140a according to one embodiment of the present invention, the culture may be performed under a condition maintaining a stirring speed of 250 rpm to 350 rpm, a culture temperature of 23° C. to 27° C., and a pH of 6.8 to 7.2.

In addition, according to one embodiment of the present invention, gas obtained by mixing air with oxygen at the ratio of 9:1 to 11:1 may be supplied into a fermentation tank for culturing the *Phaffia rhodozyma* at a rate of 4 vvm to 6 vvm.

Meanwhile, according to one embodiment of the present invention, the culture may be performed under light conditions of 4,000 lx to 8,000 lx, more preferably 5,500 lx to 6,500 lx.

Figure 5:
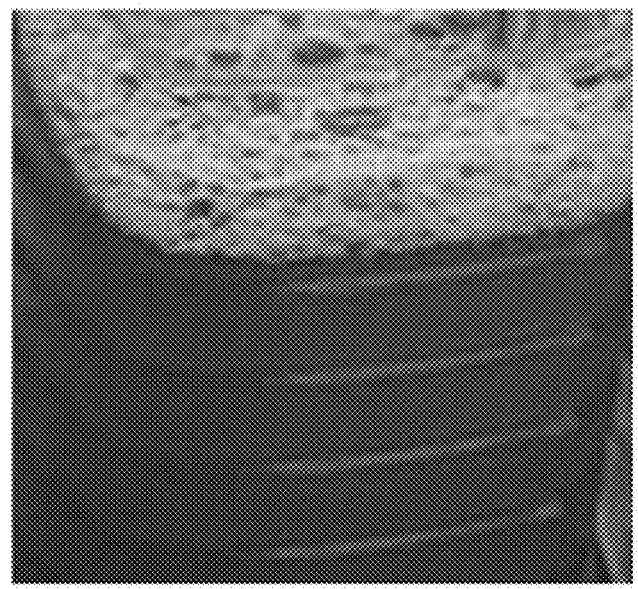
FIG. 5 is a diagram schematically showing a mutant selection process of *Dunaliella* according to one embodiment of the present invention.
Figure 5:
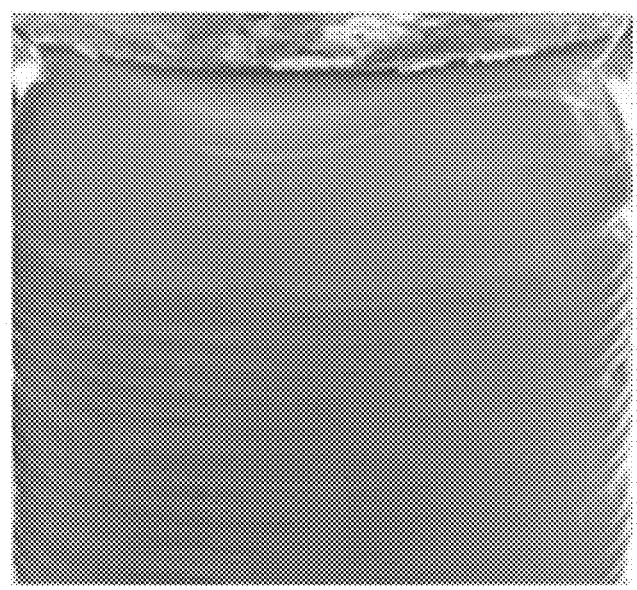
Figure 6:
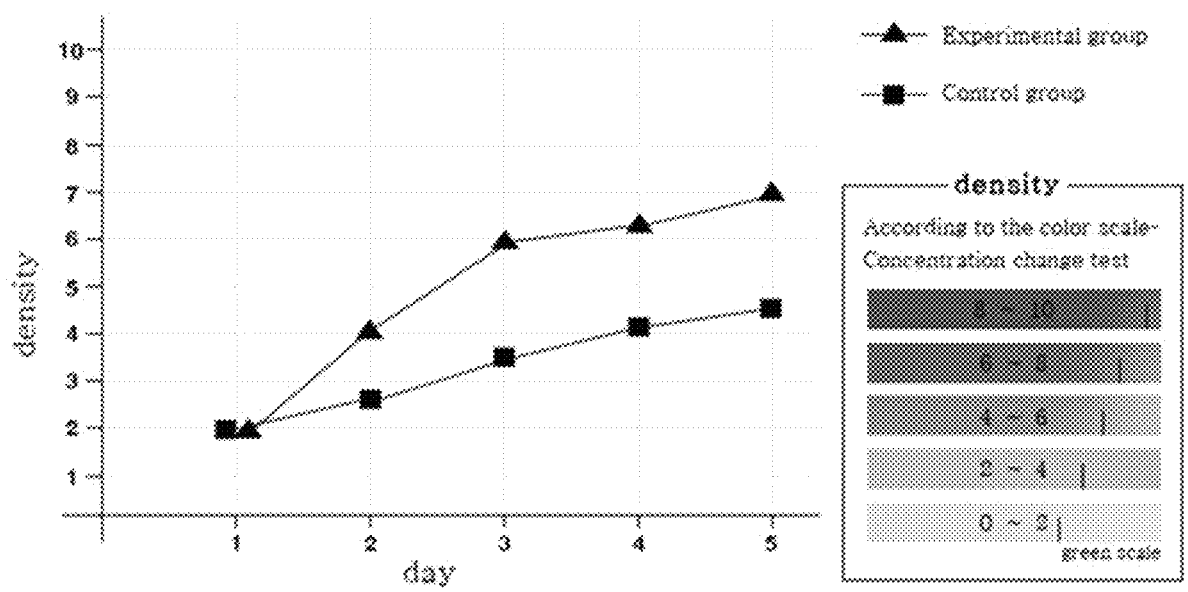
FIG. 6 is a graph schematically showing a culture rate of *Phaffia rhodozyma* subject to the microalgae culturing step according to one embodiment of the present invention.
Figure 7:
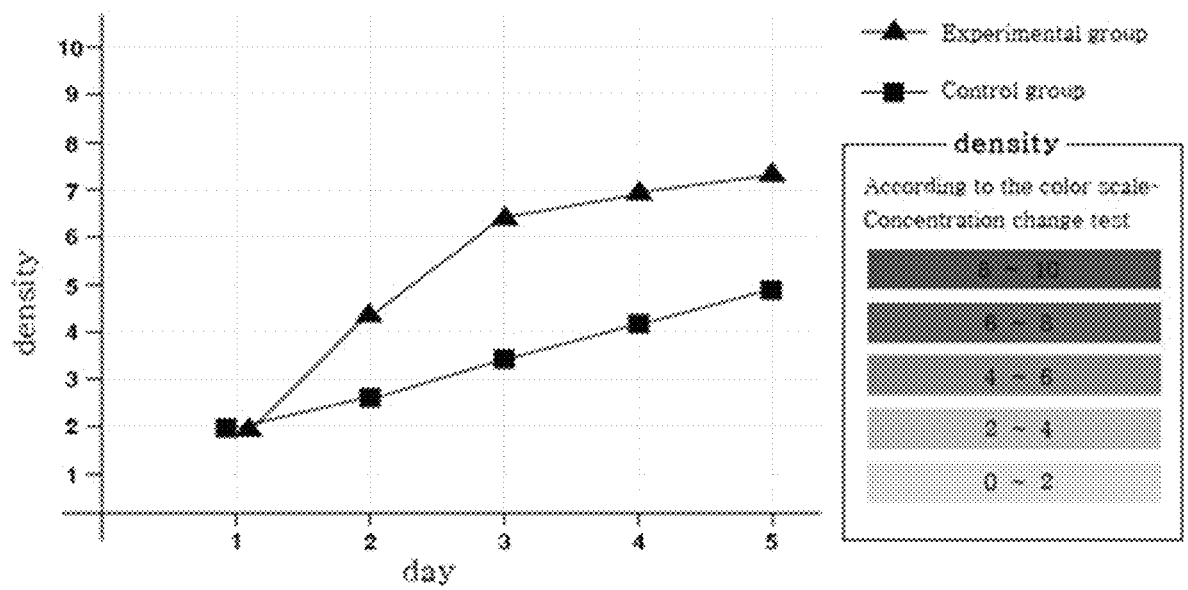
FIG. 7 is a graph schematically showing a culture rate of *Dunaliella salina* subject to the microalgae culturing step according to one embodiment of the present invention.
Figure 8:
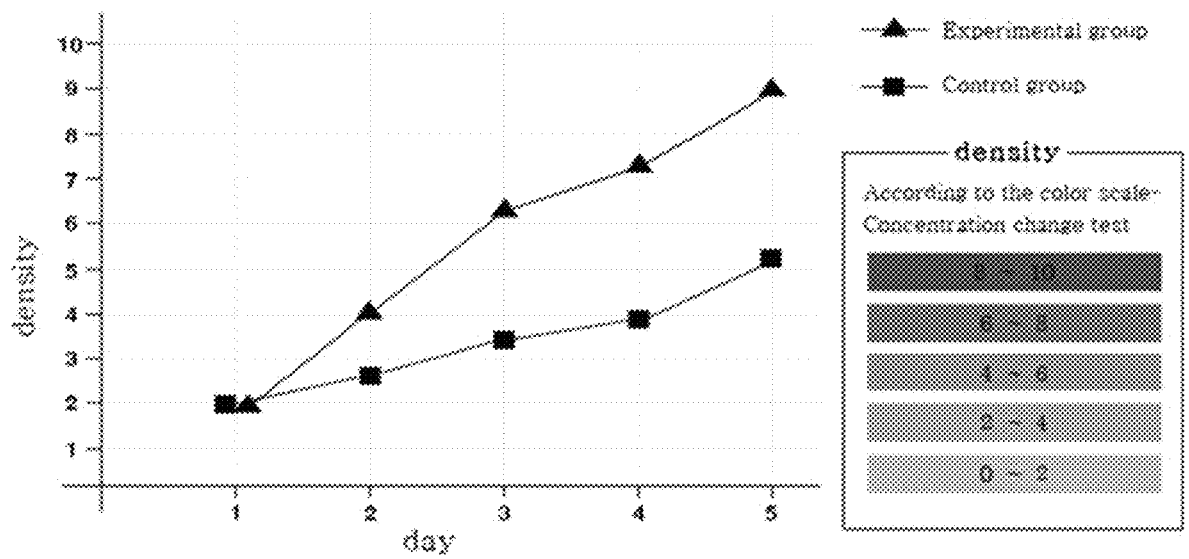
FIG. 8 is a graph schematically showing a culture rate of *Chlorella vulgaris* subject to the microalgae culturing step according to one embodiment of the present invention.
Figure 9:
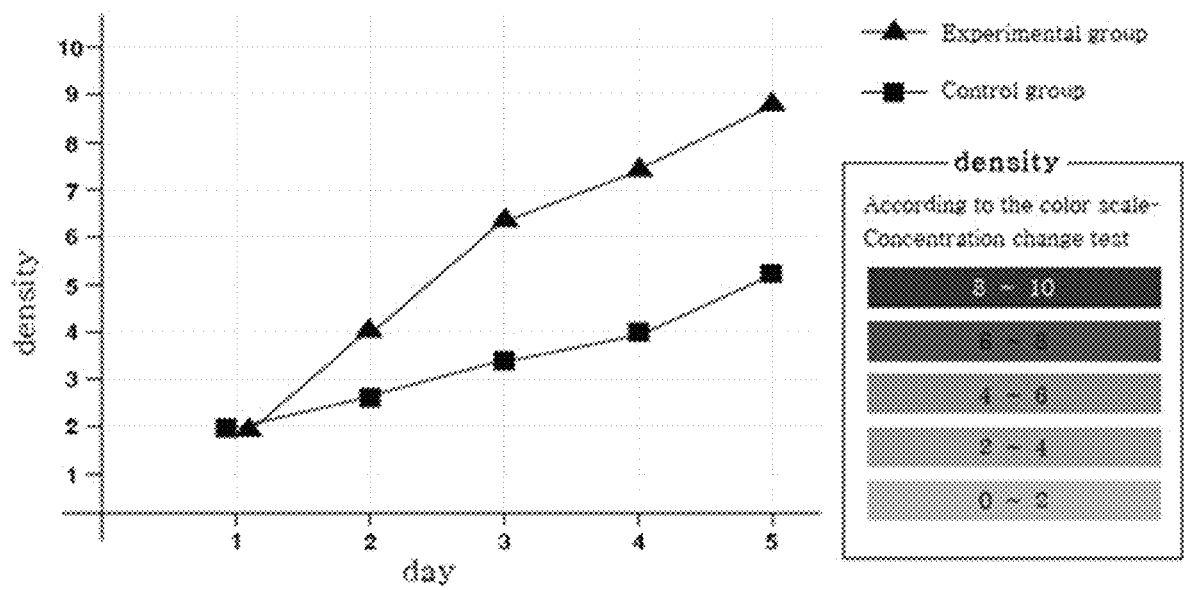
FIG. 9 is a graph schematically showing a culture rate of *Spirulina platensis* subject to the microalgae culturing step according to one embodiment of the present invention.

FIG. 5 is a diagram schematically showing a mutant selection process of *Dunaliella* according to one embodiment of the present invention.

FIG. 5(a) shows a state of *Dunaliella salina* strain before performing the mutation promoting step S110a, and FIG. 5(b) shows a state of *Dunaliella salina* strain after applying light stress through the mutation promoting step S110a. Accordingly, it can be seen that the *Dunaliella salina* mutated through the mutation promoting step S110a according to one embodiment of the present invention changes in color by accumulating a large amount of beta-carotene in a cell.

FIGS. 6 to 9 are graphs schematically showing culture rates of *Phaffia rhodozyma, Dunaliella salina, Chlorella*

*vulgaris*, and *Spirulina platensis* subject to the microalgae culturing step, respectively, according to one embodiment of the present invention.

In the microalgae culturing step S100 according to one embodiment of the present invention, microalgae may be mass-cultured in a medium containing at least one of ionized calcium and silicic acid. As described in FIGS. 2 and 4, at least one of ionized calcium and silicic acid is containing in the media for culturing *Phaffia rhodozyma, Dunaliella salina, Chlorella vulgaris*, and *Spirulina platensis*, thereby exhibiting a higher culture rate, so that the culture efficiency may be increased.

Each of FIGS. 6 to 9 shows the culture density according to time of control groups in which *Phaffia rhodozyma, Dunaliella salina, Chlorella vulgaris*, and *Spirulina platensis* are cultured in media that do not contain ionized calcium and silicic acid, and experimental groups cultured in media to which ionized calcium and silicic acid are added, respectively. The culture density is calculated according to a color, and a culture rate may be evaluated through the culture density.

Referring to FIGS. 6 to 9, it can be seen that the density of microalgae increases rapidly in all the experimental groups compared to the control groups. Therefore, when microalgae is cultured in a medium containing at least one of ionized calcium and silicic acid according to one embodiment of the present invention, the culture efficiency can be increased.

Figure 10:
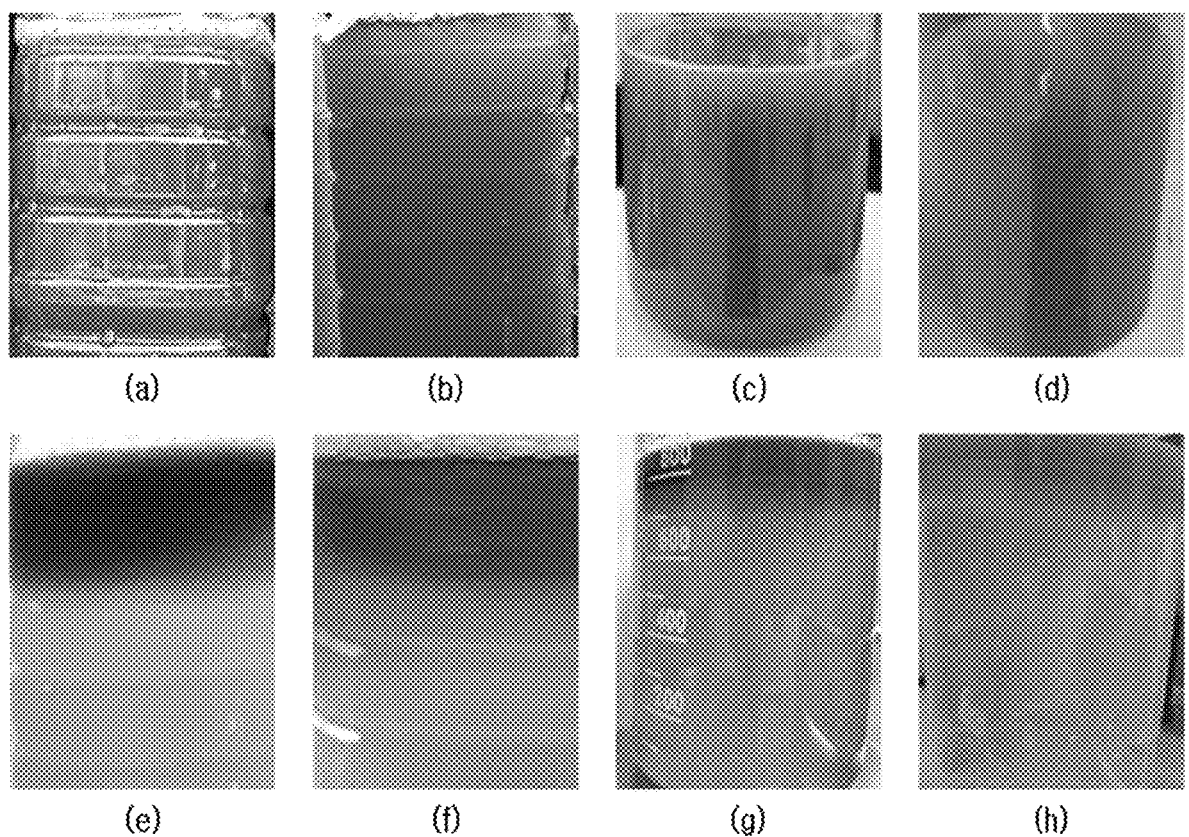
FIG. 10 is a diagram schematically showing a process of performing the microalgae collecting step according to one embodiment of the present invention.

FIG. 10 is a diagram schematically showing a process of performing the microalgae collecting step according to one embodiment of the present invention.

According to one embodiment of the present invention, in the microalgae collecting step S200, an aqueous ionized calcium solution having a content of 70 mg/L or more of calcium may be administered to culture water in which microalgae may be cultured, and microalgae floating on the surface may be collected.

Various schemes may be used to collect microalgae in a liquid medium. Centrifugation, filtration, and flocculation technologies, and the like are used to separate microalgae from the liquid medium and purify highly concentrated microalgae containing minimum water.

Although widely used as a microbial harvesting technology, the centrifugation technology requires a lot of time and high energy costs to process a large capacity, and is expensive for equipment. The filtration technology uses a mesh having a size of a micrometer (μm) unit and easily blocked by very small microorganisms, so a continuous operation is very difficult and it is not easy to apply to large capacity.

According to the present invention, the specific gravity of minerals in water is increased by dissolving ionized calcium at a high concentration in a short time in culture water into which microalgae are cultured so as to scoop microalgae becoming float on a water surface due to the increased specific gravity of water, so that the microalgae may be collected. According to the method of collecting microalgae in the above manner, the utility for collecting microalgae can be increased, the cost and the time required for the centrifugation can be relatively reduced, and a large amount of cost can be unnecessary for reusing calcium ion water having a high calcium content after collecting the microalgae.

FIG. 10 shows a state of performing the microalgae collecting step S200 according to one embodiment of the present invention. FIGS. 10($a$), 10($b$), 10($c$), and 10($d$) show states in which *Phaffia rhodozyma, Dunaliella salina, Chlorella vulgaris*, and *Spirulina platensis* are cultured in liquid media, respectively. As shown in the drawings, the four kinds of microalgae are spread uniformly in the liquid media.

FIGS. 10($e$), 10($f$), 10($g$), and 10($h$) show states in which the microalgae float to the surface by dissolving ionized calcium to the liquid media of *Phaffia rhodozyma, Dunaliella salina, Chlorella vulgaris*, and *Spirulina platensis* according to one embodiment of the present invention. In the embodiment of FIG. 10, a high concentration (80 mg/L) aqueous ionized calcium solution of 100 ml per 1 L was administered to allow the microalgae to float.

Figure 11:
FIG. 11 is a diagram schematically showing states of performing an oil extracting step and a powder processing step according to one embodiment of the present invention.
Figure 11:
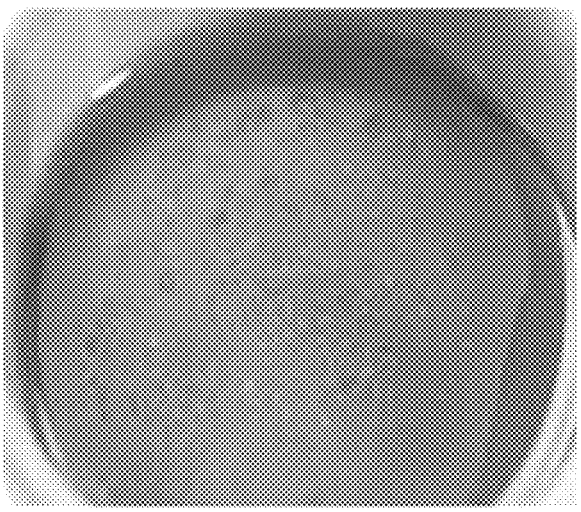
Figure 11:
Figure 11:

FIG. 11 is a diagram schematically showing states of performing an oil extracting step and a powder processing step according to one embodiment of the present invention.

In the oil extracting step S300 according to one embodiment of the present invention, oil may be extracted from the microalgae by physical compression.

A compression, an enzyme treatment, a solvent extraction, a microwave, hot water extraction, and the like may be used as schemes for extracting oil from microalgae. Since the compression among the above schemes is a physical scheme that does not include a chemical substance, the purest oil may be obtained.

According to one embodiment of the present invention, the compression is performed through a horizontal ball mill system to destroy cell walls of microalgae, so that oil may be extracted. The oil extracted in the above manner is shown in FIGS. 11($a$) and 11($b$).

Meanwhile, in the powder processing step S400 according to one embodiment of the present invention, the remaining microalgae after extraction of the oil are processed into powder. Cells of the microalgae may have a size of about 5 μm to 15 μm. According to one embodiment of the present invention, the microalgal cells may be processed into nano-powder of 3 μm or less to facilitate a penetration performance of functional ingredients into a human body or an animal body when being eaten.

The microalgae micro powder prepared according to one embodiment of the present invention contains functional ingredients such as astaxanthin, lutein, zeaxanthin, beta-carotene, omega-3, DHA, and EPA.

A plurality of experiments were conducted as follows in order to prove the effect of the above functional ingredients of the present invention.

Experimental Results of the Present Invention
(Production Management Experiment on Broiler Chickens)

First, an experiment for measuring the growth of edible chickens (broilers) was conducted to measure and verify the improvement of antioxidant and immunity by the microalgae micro powder according to one embodiment of the present invention.

1. Common Experimental Conditions

Target species and breeding period: chicks were hatched in the same incubation facility and placed in a farm. The target species was a general broiler breed raised in Korea. The evaluation was conducted after rearing for 31 days.

Breeding density: 1,000 broilers for each of an experimental group and a control group were provided in the same henhouses in an area of 25 pyeong.

Facilities: The facilities were heated at a predetermined temperature to raise the chicks, and the rearing was carried out in modern breeding management facilities equipped with an automatic feeder, automatic waterer, and the like.

Feed: The same general broiler feed products were selected and fed. However, since the growth rates between the experimental group and the control group were different from each other, the digestion rates were different from each other. Thus, there was a difference in amounts of feeding (Microalgae micro powder was added to the feed of the experimental group).

Feeding when the chicks are placed in the farm: The feed was supplied after a sufficient number of chicks were allowed to drink water for 2 to 3 hours. After 4 to 5 hours of supplying the feed, chicks were randomly selected and inspected by checking whether the chicks have eaten the feed by touching crop sacs. In addition, the feed was supplied while checking whether the feed has been digested. For 2 to 3 days after providing the chicks, the feed was mixed with water, held with hands, and released to be scattered again, and the feed soaked for 1 to 2 hours was scattered on a paper at the bottom, or supplied by using an auxiliary feeder (the feed mixed with water was supplied 6 to 7 times a day for 2 to 3 days).

TABLE 1

| Weight (g) | Accumulated amounts of feed intake (g) | Feed conversion rate (FCR) |
|---|---|---|
| 137 | 135 | 0.99 |
| 314 | 435 | 1.26 |
| 687 | 1,005 | 1.46 |
| 1,114 | 1,767 | 1.59 |
| 1,585 | 2,694 | 1.70 |

Temperature and humidity management: The temperature and humidity management is a factor that most affects the feed conversion rate. When the temperature is low, the chicks try to compensate for body heat loss by increasing feed intake, and when the temperature is excessively higher, the fuel cost is increased and the generation of ammonia gas is also increased. Accordingly, the appropriate temperature and humidity management for each age was conducted as follows (a shell refers to a device as a heat source in the farm, which allows a chick to control a body temperature by approaching or going away from the heat source when feeling cold).

TABLE 2

| Item | | Placed in the farm | Week 1 | Week 2 | Week 3 | Week 4 | Week 5 |
|---|---|---|---|---|---|---|---|
| Temperature (° C.) | In shell | 35 | 32 | 29 | 26 | 23 | 23 |
| | Indoors | 28 | 26 | 24 | 22 | 10 | 10 |
| Humidity (%) | | 75 | 70 | 65 | 65 | 63 | 60 |

Other management: It is important to keep a feed container and a water container clean above all. The water container was washed daily with water and regularly disinfected by a disinfectant combined with drinking water. To secure a feeding space sufficient for the chick period is required for the feeding management. The auxiliary feeders started to be removed from 5 to 7 day ages and were completely removed at 10 day ages. When the feeder is highly located, the uniformity and the feed conversion rate become poor. After straws spread around the feeder are checked, the height of the feeder was often adjusted to be the same as the height of a back of the chick. The amount of feed in the feeder was maintained at ⅓ or less, so that the loss of feed was reduced. Feed intake was stimulated by frequently operating the feeder.

2. Experimental Conditions on Experimental Group

The broilers were fed and managed under the same conditions as the control group, but only the feed mixture additives were differentiated. "Microalgae micro powder" as a feed additive was added to the feed of the experimental group. The microalgae micro powder of 10 kg per ton of blended feed was mixed and used.

3. Experimental Conditions on Control Group

The broiler feeding management was performed without modification in the above common experimental conditions and compared with the experimental group.

Figure 12:
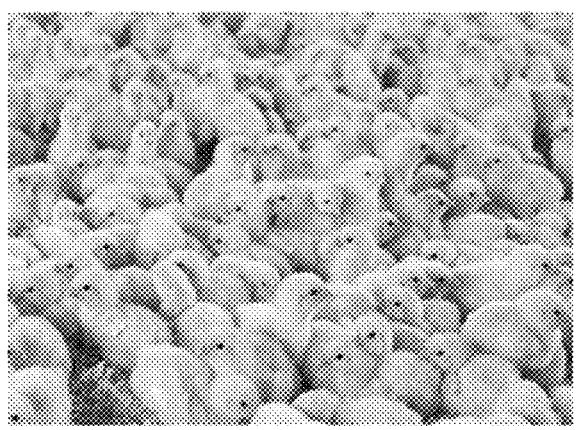
FIG. 12 is a diagram schematically showing an experiment process of a broiler production management to confirm the effectiveness of microalgae micro powder according to one embodiment of the present invention.
Figure 12:
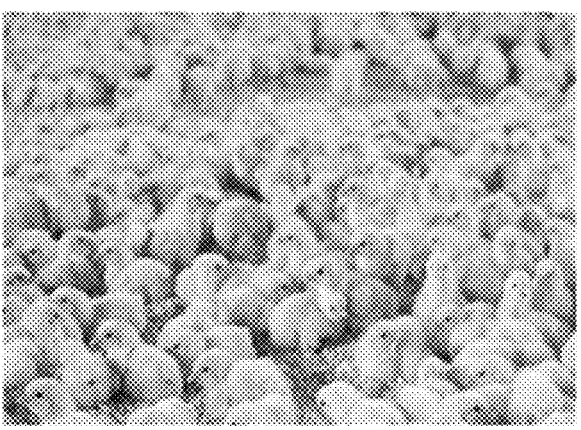
Figure 12:
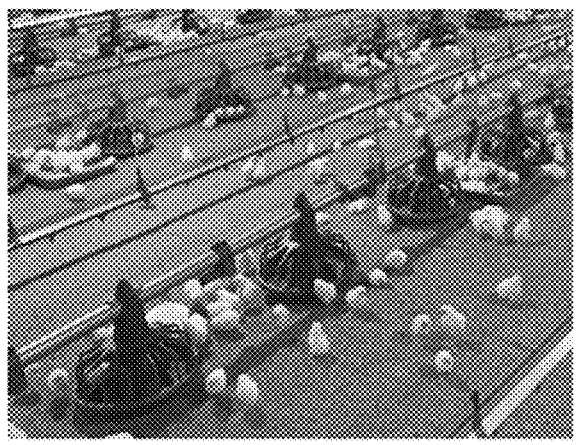
Figure 12:
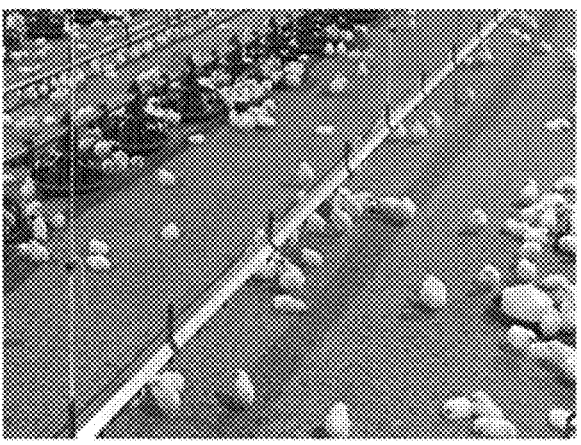
Figure 13:
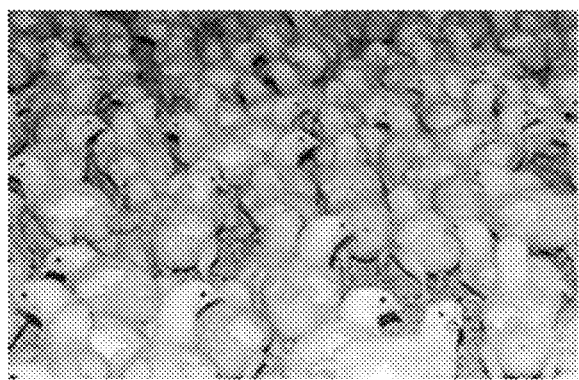
FIG. 13 is a diagram schematically showing an experiment process of a broiler production management to confirm the effectiveness of microalgae micro powder according to one embodiment of the present invention.
Figure 13:
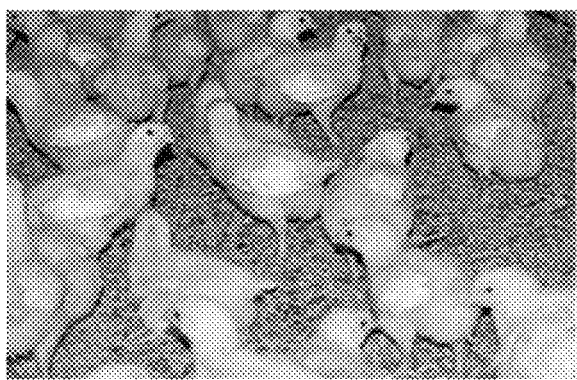
Figure 13:
Figure 13:

FIGS. 12 and 13 are diagrams schematically showing an experiment process of a broiler production management to confirm the effectiveness of microalgae micro powder according to one embodiment of the present invention.

FIG. 12(a) shows chicks placed in a henhouse of the control group, FIG. 12(b) shows chicks placed in a henhouse of the experimental group, FIG. 12(c) shows a state of the henhouse of the control group, and FIG. 12(d) shows a state of the henhouse of the experimental group.

Meanwhile, FIG. 13(a) shows a state of 1-week-old chicks in the control group, and FIG. 13(b) shows a state of 1-week-old chicks in the experimental group.

As a result of evaluating the 31-week-old chicks in the experimental group and the control group after the chicks are placed in the farm, there was no significant difference in developmental state, but the sizes seemed different when viewed with naked eyes. In addition, the chicks in the experimental group were observed as having the feed consumption that is 7% higher. In addition, when evaluated on the 7th day after placed in the farm, the control group had an average weight of about 140 g and the experimental group had about 160 g, which shows a large difference in weight of 20 g. Based on 7% of the amount of feed consumption while the difference in weight was 20 g, the evaluation result indicates that the nutrient absorption rate of chicks in the experimental group has increased even by the same amount of feed. The incidence of weak chick (referring to a chick having relatively small size in the group) or deformed chick was similar, ranging from 0.5% to 1%.

Meanwhile, FIG. 13(c) shows a state of 31-week-old chicks in the control group, and FIG. 13(d) shows a state of 31-week-old chicks in the experimental group.

As a result of evaluating the 31-week-old chicks in the experimental group and the control group after the chicks are placed in the farm, a difference in size was observed even with naked eyes, and there was also a difference in activities of the chicks. Particularly, there was a remarkable difference in reaction when the feeder was operated and a feeding sound was generated. All of the 11 weak chicks (having relatively small size in the group) or deformed chicks of the control group were dead and disposed. Meanwhile, all of the 13 weak chicks generated in the experimental group survived though the growth rate was low. In addition, the biggest difference was the difference in hair loss. While the chicks in the control group were small in size and had missing hairs in several spots, the chicks in the experimental group had hairs uniformly grown so as to exhibit a healthy appearance even at a glance.

Table 3 compares the growth rates by week age between the experimental group and the control group as follows.

TABLE 3

| Item | 1-week-old | 2-week-old | 3-week-old | 4-week-old | 31-week-old |
|---|---|---|---|---|---|
| Control | 140 | 350 | 810 | 1,370 | 1,480 |

TABLE 3-continued

| Item | 1-week-old | 2-week-old | 3-week-old | 4-week-old | 31-week-old |
|---|---|---|---|---|---|
| group (kg) | | | | | |
| Experimental group (kg) | 160 | 390 | 860 | 1,570 | 1,680 |

As shown in Table 3, it is confirmed that the experimental group had the growth rate higher than that of the control group. In addition, body compositions of grown chickens were analyzed and compared through feeding experiments. Tables 4 and 5 summarize body compositions of the control group and the experimental group as follows. Each nutritional ingredient is indicated as a content per 100 g.

TABLE 4

Table on body composition analysis of control group

| Niacin | Natrium | Protein | Carbohydrate | Retinol |
|---|---|---|---|---|
| 11.10 mg | 64.80 mg | 23.00 g | 0.00 g | 0.00 µg |
| Beta-carotene | Vitamin A | Vitamin B1 | Vitamin B2 | Vitamin B6 |
| 0.00 µg | 5.10 µgRE | 0.06 mg | 0.07 mg | 0.50 mg |
| Vitamin C | Vitamin E | Dietary Fiber | Zinc | Folic acid |
| 1.10 mg | 0.15 mg | 0.00 g | 0.70 mg | 3.80 µg |
| Phosphorus | Lipid | Iron | Potassium | Calcium |
| 192.00 mg | 1.10 g | 0.80 mg | 245.00 mg | 13.00 mg |
| Omega-3 fatty acids | Omega-6 fatty acids | Cholesterol | | |
| 0.25% min | 2.30% min | 78.00 mg | | |

TABLE 5

Table on body composition analysis of experimental group

| Niacin | Natrium | Protein | Carbohydrate | Retinol |
|---|---|---|---|---|
| 8.30 mg | 61.58 mg | 20.80 g | 0.25 g | 3.70 µg |
| Beta-carotene | Vitamin A | Vitamin B1 | Vitamin B2 | Vitamin B6 |
| 0.00 µg | 26.00 µgRE | 8.35 µgRE | 0.17 mg | 0.27 mg |
| Vitamin C | Vitamin E | Dietary Fiber | Zinc | Folic acid |
| 0.80 mg | 0.35 mg | 0.00 g | 0.58 mg | 4.86 µg |
| Phosphorus | Lipid | Iron | Potassium | Calcium |
| 206.50 mg | 2.70 g | 0.92 mg | 287.10 mg | 31.85 mg |
| Omega-3 fatty acids | Omega-6 fatty acids | Cholesterol | Ge | Ash |
| 3.7% min | 0.6% min | 32.45 mg | 0.03 mg | 2.70 g |

Meanwhile, the chicks in the experimental group obtained through this experiment according to one embodiment of the present invention were monitored for the effectiveness as an SPF product. Table 6 summarizes the SPF monitoring test method for the chicks in the experimental group as follows.

TABLE 6

| Item | Pathogen | Inspection method (test method) |
|---|---|---|
| Virus | Avian adenovirus, group 1 | ELISA inspection method (ELISA kit) |
| | Avian encephalomyelitis virus | |
| | Infectious bursal disease virus | ELISA serum antibody monitoring |
| | Avian infectious bronchitis virus | |
| | Influenza A Virus | Five subjects were randomly selected and monitored from the experimental group. |
| | Avian infectious laryngotracheitis virus | |
| | Marek's disease virus | |
| | Newcastle disease virus | |
| | Avian nephritis virus | |

TABLE 6-continued

| Item | Pathogen | Inspection method (test method) |
|---|---|---|
| | Chicken anaemia virus | |
| Bacteria | Mycoplasma gallisepticum | PCR test method |
| | Mycoplasma synoviae | |
| | Salmonella pullorum | |

Table 7 summarizes the results of SPF monitoring the chicks in the experimental group as follows.

TABLE 7

| Avian adenovirus, group 1 | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
|---|---|
| Avian encephalomyelitis virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Infectious bursal disease virus | ① Inspection method<br>Serum antibody ELISA inspection<br>ELISA kit<br>Protocol of manufacturer |

TABLE 7-continued

| | |
|---|---|
| Avian infectious bronchitis virus | ② Inspection result<br>Number of samples: n = 5 (M001, M002, M003, M004, M005)<br>All negative<br>① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Influenza A Virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Avian infectious laryngotracheitis virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Marek's disease virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Newcastle disease virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Avian nephritis virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Chicken anaemia virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Mycoplasma gallisepticum | ① Inspection method—PCR conditions condition<br>94° C. 2 min<br>94° C. 30 sec, 53° C. 30 sec, 68° C. 40 sec (32 cycle)<br>4° C. ∞<br>sample: nasal swab<br>② Inspection result<br>Number of samples: n = 5 (M001, M002, M003, M004, M005)<br>As a result of the inspection,<br>Mycoplasma gallisepticum was not detected in all samples. |
| Mycoplasma synoviae | ① Inspection method—PCR conditions condition<br>94° C. 2 min<br>94° C. 30 sec, 56° C. 30 sec, 68° C. 40 sec (32 cycle)<br>4° C. ∞<br>sample: nasal swab<br>② Inspection result<br>Number of samples: n = 5 (M001, M002, M003, M004, M005)<br>As a result of the inspection,<br>Mycoplasma synoviae was not detected in all samples. |
| Salmonella pullorum | ① Inspection method—PCR conditions condition<br>94° C. 2 min<br>94° C. 30 sec, 55° C. 30 sec, 68° C. 40 sec (32 cycle)<br>4° C. ∞<br>sample: nasal swab<br>② Inspection result<br>Number of samples: n = 5 (M001, M002, M003, M004, M005)<br>As a result of the inspection,<br>Salmonella pullorum was not detected in all samples. |

As the results of various virus and bacteria monitoring tests on the chicks in the experimental group, any abnormality was not observed in all monitoring results.

Experimental Results of the Present Invention (Production Management Experiment on Layer Chicken)

Next, an experiment for measuring the growth of edible chickens (broilers) was conducted to measure and verify the improvement of antioxidant and immunity by the microalgae micro powder according to one embodiment of the present invention.

1. Common Experimental Conditions

Target species and breeding period: chicks were hatched in the same incubation facility and placed in the farm. The target species was a general White Leghorn breed raised in Korea. The evaluation was performed after rearing for 32 weeks.

Breeding density: 300 White Leghorn chicks for each of an experimental group and a control group were placed in the same henhouses in an area of 25 pyeong.

Facility: The facilities were heated at a predetermined temperature to raise the chicks, and the test was carried out in a modern breeding management facility equipped with an automatic feeder, automatic waterer, and the like.

Feed: The same general layer feed products were selected and fed. However, since the growth rates between the experimental group and the control group were different from each other, the digestion rates were different from each other. Thus, there was a difference in amounts of feeding (Microalgae Micro Powder was Added to the Feed of the Experimental Group).

Feeding management from the beginning to 6 week age: Broiler electric feed was performed. Six weeks are important period for the development of immune organs, skeletons, and major organs (such as lungs, respiratory organs, digestive organs, heart, liver, and kidneys). A careful feeding management is important because a weight growth up to 6 week age affects a metabolic function and an egg shell quality during breeding period. The temperature was maintained at 35° C. or higher for 3 days after beginning at the farm.

Temperature and humidity management: The temperature and humidity management is a factor that most affects the feed conversion rate. When the temperature is low, the chicks try to compensate for body heat loss by increasing feed intake, and when the temperature is excessively higher, the fuel cost is increased and the generation of ammonia gas is also increased. Accordingly, the appropriate temperature and humidity management for each age was conducted as Table 2 of the production management experiment on broiler chickens Feeding management during 6 to 8 week ages: It is the time for developing 85% of the skeleton. The feeding management is the same as the steps of feeding broilers, such as maintaining a sufficient living area.

Feeding management during 8 to 9 week ages: It is the time when an ovarian development begins. A control of sexual maturity inhibition started, and scheduled lighting was conducted in a dark room. The lighting time during growing period is related to the inhibition of the ovarian development. The lighting was supplied for 10 hours from 8 week ages, and the luminous intensity was set to 10 lux to 15 lux.

Feeding management during 9 to 15 week ages: It is the time for developing 95% of the skeleton. Likewise, it was focused on maintaining the lighting time maintenance (inhibiting the sexual maturity).

Feeding management during 15 to 17 week ages: It is the time when the ovary is rapidly developed and a sex hormone secretion is increase, and calcium deposition of the skeleton begins, in which a comb becomes red and large. Likewise, it was focused on maintaining the lighting time maintenance (inhibiting the sexual maturity).

Feeding management during 17 to 27 week ages: The sexual maturity inhibition was released through the lighting stimulation when a weight reached 1.4 kg to 1.48 kg from 120 to 126 day ages. This is the time when breeding organs rapidly develop and a weight gain starts. This is the time when an initial breeding starts (breeding season 1). The feed was changed into feed for the beginning of breeding and sufficiently supplied. The lighting was gradually increased up to 16 hours per day for the lighting stimulation. Late-night lighting and late-night feeding were provided. Accordingly, the amount of feed intake was increased. The above process was performed until at least 27 week ages, which is a period when the immunity of the chickens is lowered to the lowest level and a disease is easily generated.

Feeding management during 27 to 30 week ages: This is an intermediate breeding period when a body maturation is completed. It is a period when an amount of breeding of one chicken per day is almost unchanged since the breeding rate is gradually decreased but the egg weight keeps increasing. The feed was changed into feed for the intermediate breeding period (to increase a content of calcium in the feed).

Eggs obtained within the breeding period: Eggs obtained at 23 week ages were collected and evaluated to evaluate the quality of corresponding products from the experimental group and the control group.

2. Experimental Conditions on Experimental Group

The layer chickens were fed and managed under the same conditions as the control group, but only the feed mixture additives were differentiated. "Microalgae micro powder" as a feed additive was added to the feed of the experimental group. The microalgae micro powder of 10 kg per ton of blended feed was mixed and used.

3. Experimental Conditions on Control Group

The broiler feeding management was performed without modification in the above common experimental conditions and compared with the experimental group.

Figure 14:
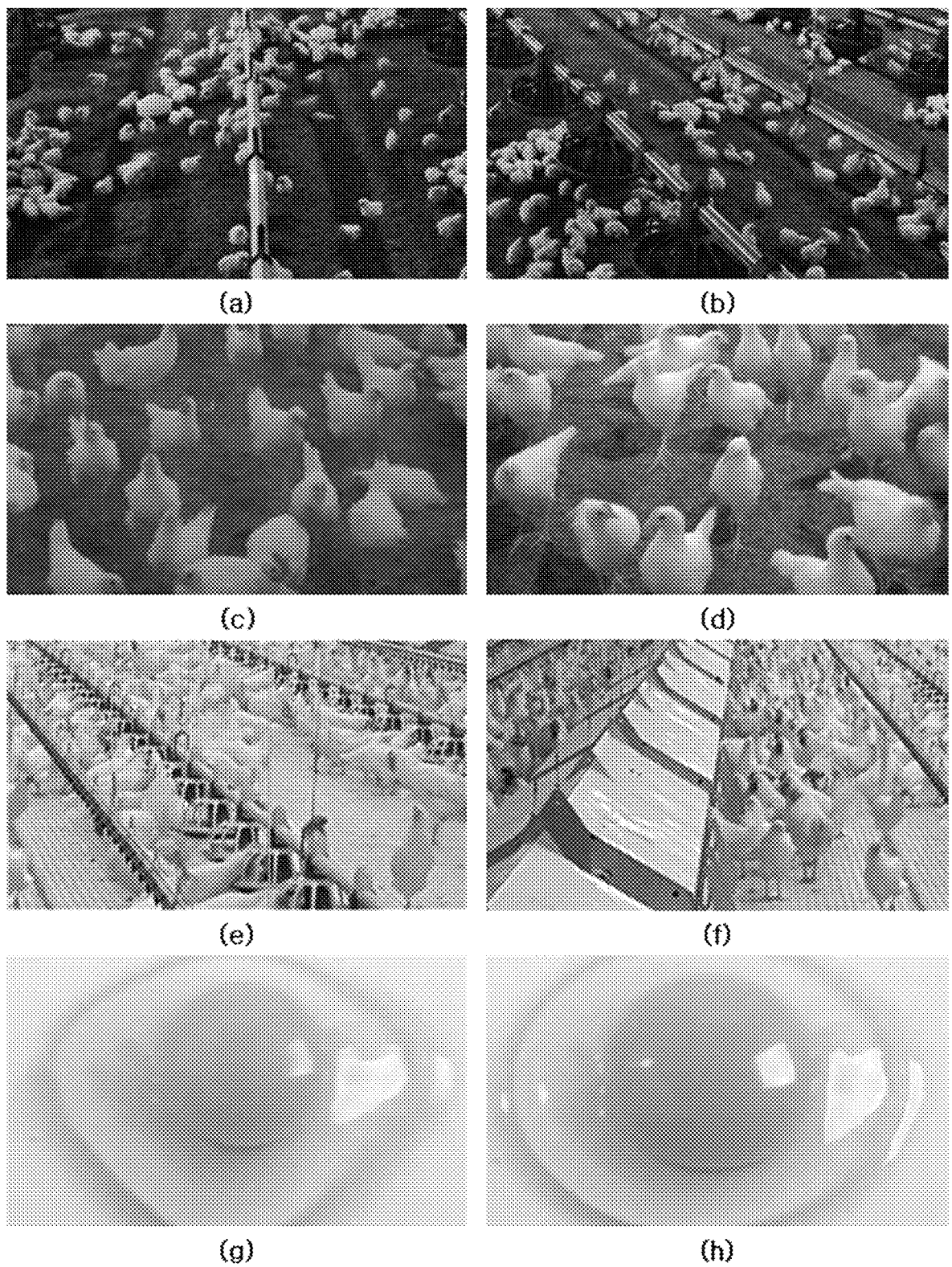
FIG. 14 is a diagram schematically showing an experiment process of a layer chicken production management to confirm the effectiveness of microalgae micro powder according to one embodiment of the present invention.

FIG. 14 is a diagram schematically showing an experiment process of a layer chicken production management to confirm the effectiveness of microalgae micro powder according to an embodiment of the present invention.

FIG. 14(a) shows chicks placed in a henhouse of the control group. FIG. 14(b) shows chicks placed in a henhouse of the experimental group. FIG. 14(c) shows a state of 5-week-old layer chicken in the control group. FIG. 14(d) shows a state of 5-week-old layer chicken in the experimental group. FIG. 14(e) shows a state of 20-week-old layer chicken in the control group. FIG. 14(f) shows a state of 20-week-old layer chicken in the experimental group. FIG. 14(g) shows a state of 23-week-old layer chicken in the control group. FIG. 14(h) shows a state of 23-week-old layer chicken in the experimental group.

Functional ingredients contained in the egg obtained through the above feeding experiments were analyzed and compared.

Tables 8 and 9 summarize nutritious ingredients of the eggs obtained from the control group and the experimental group as follows. Each nutritional ingredient is indicated as a content per 100 g.

TABLE 8

Table on functional ingredients of egg in control group

| Niacin | Natrium | Protein | Carbohydrate | Retinol |
|---|---|---|---|---|
| 0.50 mg | 132.50 mg | 11.70 g | 3.15 g | 85.50 µg |
| Beta-carotene | Vitamin A | Vitamin B1 | Vitamin B2 | Vitamin B6 |
| 0.00 µg | 82.00 µgRE | 0.17 mg | 0.62 mg | 0.00 mg |
| Vitamin C | Vitamin E | Dietary Fiber | Zinc | Folic acid |
| 0.00 mg | 0.00 mg | 1.50 g | 1.10 mg | 0.00 µg |
| Phosphorus | Lipid | Iron | Potassium | Calcium |
| 178.00 mg | 8.10 g | 1.20 mg | 145.00 mg | 48.00 mg |
| Omega-3 fatty acids | Omega-6 fatty acids | Cholesterol | | |
| 0.12% min | 2.27% min | 434.05 mg | | |

TABLE 9

Table on functional ingredients of egg in experimental group

| Niacin | Natrium | Protein | Carbohydrate | Retinol |
|---|---|---|---|---|
| 1.64 mg | 207.2 mg | 27.00 g | 2.95 g | 109.50 µg |

TABLE 9-continued

Table on functional ingredients of egg in experimental group

| Niacin | Natrium | Protein | Carbohydrate | Retinol |
|---|---|---|---|---|
| Beta-carotene | Vitamin A | Vitamin B1 | Vitamin B2 | Vitamin B6 |
| 625.15 μg | 114.00 μgRE | 2.80 μgRE | 1.90 mg | 0.17 mg |
| Vitamin C | Vitamin E | Dietary Fiber | Zinc | Folic acid |
| 0.70 mg | 0.08 mg | 2.60 g | 2.85 mg | 0.00 μg |
| Phosphorus | Lipid | Iron | Potassium | Calcium |
| 227.10 mg | 13.00 g | 1.95 mg | 308.00 mg | 77.20 mg |
| Omega-3 fatty acids | Omega-6 fatty acids | Cholesterol | Ge | Ash |
| 2.95% min | 0.28% min | 428.55 mg | 0.10 mg | 1.20 g |
| DHA | EPA | Astaxanthin | Lutein | Zeaxanthin |
| 0.73 mg | 0.35 mg | 0.19 mg | 0.15 mg | 0.08 mg |

Meanwhile, the eggs in the experimental group obtained through this experiment according to one embodiment of the present invention were monitored for effectiveness as an SPF product.

Table 10 summarizes the SPF monitoring test method for the eggs in the experimental group as follows.

TABLE 10

| Item | Pathogen | Inspection method (test method) |
|---|---|---|
| Virus | Avian adenovirus, group 1<br>Avian encephalomyelitis virus<br>Infectious bursal disease virus<br>Avian infectious bronchitis virus<br>Influenza A Virus<br>Avian infectious laryngotracheitis virus<br>Marek's disease virus<br>Newcastle disease virus<br>Avian nephritis virus<br>Chicken anaemia virus | ELISA inspection method (ELISA kit)<br>ELISA serum antibody monitoring<br>Ten subjects were randomly selected and monitored from the experimental group. |
| Bacteria | *Mycoplasma gallisepticum*<br>*Mycoplasma synoviae*<br>*Salmonella pullorum* | PCR test method |

Table 11 summarizes the results of SPF monitoring the eggs in the experimental group as follows.

TABLE 11

| Avian adenovirus, group 1 | ① Inspection method<br>Serum antibody ELISA inspection<br>ELISA kit<br>Protocol of manufacturer<br>② Inspection result<br>Number of samples: n = 10 (M001, M002, M003, M004, M005, M006, M007, M008, M009, M010)<br>All negative |
|---|---|
| Avian encephalomyelitisvirus | ① Inspection method<br>Serum antibody ELISA inspection<br>ELISA kit<br>Protocol of manufacturer<br>② Inspection result<br>Number of samples: n = 10 (M001, M002, M003, M004, M005, M006, M007, M008, M009, M010)<br>All negative |
| Infectious bursal disease virus | ① Inspection method<br>Serum antibody ELISA inspection<br>ELISA kit<br>Protocol of manufacturer<br>② Inspection result<br>Number of samples: n = 10 (M001, M002, M003, M004, M005, M006, M007, M008, M009, M010)<br>All negative |
| Avian infectious bronchitis virus | ① Inspection method<br>Serum antibody ELISA inspection<br>ELISA kit<br>Protocol of manufacturer<br>② Inspection result<br>Number of samples: n = 10 (M001, M002, M003, M004, M005, M006, M007, M008, M009, M010)<br>All negative |
| Influenza A Virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Avian infectious laryngotracheitis virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Marek's disease virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Newcastle disease virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Avian nephritis virus | ① Inspection method<br>Serum antibody ELISA inspection<br>ELISA kit<br>Protocol of manufacturer<br>② Inspection result<br>Number of samples: n = 5 (M001, M002, M003, M004, M005)<br>All negative |
| Chicken anaemia virus | ① Inspection method<br>Serum antibody ELISA inspection<br>ELISA kit<br>Protocol of manufacturer<br>② Inspection result<br>Number of samples: n = 5 (M001, M002, M003, M004, M005) |

TABLE 11-continued

| | |
|---|---|
| Mycoplasma gallisepticum | All negative<br>① Inspection method<br>PCR conditions<br>condition<br>94° C. 2 min<br>94° C. 30 sec, 53° C. 30 sec, 68° C. 40 sec (32 cycle)<br>4° C. ∞<br>sample: nasal swab<br>② Inspection result<br>Number of samples: n = 5 (M001, M002, M003, M004, M005)<br>As a result of the inspection, Mycoplasma gallisepticum was not detected in all samples. |
| Mycoplasma synoviae | ① Inspection method<br>PCR conditions<br>condition<br>94° C. 2 min<br>94° C. 30 sec, 56° C. 30 sec, 68° C. 40 sec (32 cycle)<br>4° C. ∞<br>sample: nasal swab<br>② Inspection result<br>Number of samples: n = 5 (M001, M002, M003, M004, M005)<br>As a result of the inspection, Mycoplasma synoviae was not detected in all samples. |
| Salmonella pullorum | ① Inspection method<br>PCR conditions<br>condition<br>94° C. 2 min<br>94° C. 30 sec, 55° C. 30 sec, 68° C. 40 sec (32 cycle)<br>4° C. ∞<br>sample: nasal swab<br>② Inspection result<br>Number of samples: n = 5 (M001, M002, M003, M004, M005)<br>As a result of the inspection, Salmonella pullorum was not detected in all samples. |

As the results of various virus and bacteria monitoring tests on the eggs in the experimental group, any abnormality was not observed in all monitoring results.

Experimental Results of the Present Invention (Production Management Experiment on Pigs)

Next, an experiment for measuring the growth of experimental mini pigs was conducted to measure and verify the improvement of antioxidant and immunity by the microalgae micro powder according to one embodiment of the present invention.

1. Common Experimental Conditions

Target species and breeding period: Four weaning pigs among species incubated in the same incubation facility and aseptically managed for 15 days were selected and tested. Göttingen-based mini pigs were used as a target species. The evaluation was performed after rearing for 200 day ages.

Selection of subject: Since the experimental group and the control group are required to be subject to the same conditions prior to the beginning of breeding experiment, four subjects maximally identical to each other were selected through the subject selection as shown in Table 12 below, in which the experiment was conducted with 2 subjects in the experimental group and 2 subjects in the control group.

TABLE 12

| Item | Inspection items | Detailed criteria for subject selection |
|---|---|---|
| Vital sign | Body temperature | Subjects having a standard rectal temperature of 37° C. to 39° C. were selected. |
| | Heart rate | Subjects having a standard heart rate of 70 to 160 beats upon auscultation were selected. |
| | Respiratory rate | Subjects having a standard respiratory rate of 10 to 30 breaths upon auscultation of respiratory sounds were selected. |
| | Weight | Standard subjects within 1.5 kg were selected. |
| | Appetite | Subjects paying attention to food were selected. |
| | Urination | Subjects having constant daily urination status and frequency were selected. |
| | Defecation | Subjects having constant daily defecation status and frequency were selected. |
| Posture | Posture | Subjects having a head which is not tilted to one side, subjects that can balance a position for themselves and do not stumble, and subjects that look comfortable when sitting down or standing up were selected. |
| State of consciousness | State of consciousness | Subjects that respond to surrounding stimuli, subjects that are not offensive to another animal or person, subjects that does not look stupid, and subjects without seizures were selected. |
| Head and neck | Structural integrity and symmetry | Subjects having symmetrical lips, subjects having a nose that is not twisted to one side, and subjects without swelling were selected. |
| | Movements of mouth | Subjects having normal masticating movements were selected. |
| Eye | Eyeball | Subjects having normal size and position, subjects having normal color and condition, subjects having eyeballs that do not show abnormal movements, and subjects having normal pupillary reflex were selected. |
| | Eyelid | Subjects having a symmetrical shape, subjects without discoloration, redness, or lump, subjects without twitch, and subjects having normal third eyelids were selected. |
| | Conjunctiva | Subjects without congestion or inflammation were selected. |
| | Epiphora | Subjects that do not shed tears in a normal time were selected. |
| Nose | Running nose | Subjects without running nose were selected. |
| Ear | Earflap | Subjects that do not scratch ears in a normal time, and subjects having a normal color were selected. (Pale = peripheral circulation disorder/yellow = jaundice) |
| | Ear canal | Subjects having external auditory canal without redness or ulcer, and subjects without exudation in the ear canal were selected. |

Feed and feeding: Solid feed for mini pigs of a J company was supplied. The feed containing vitamins A and D and iron was selected. The amount of feed for Göttingen-based mini pigs was increased by 200 g per day until 30 day ages and 100 g per month until 10 month ages up to 1 kg as the maximum feeding amount. The feed is required to contain sufficient nutrients such that the animal before maturity normally develops or the mature animal maintains a normal weight, and required to be clean and free of contaminants.

Breeding cage: The breeding cage was large enough to raise pigs having a size of 60×90×60 and a weight up to 20 to 25 kg per one pig. The pigs were moved to a breeding cage twice the size of a corresponding size from a period when the pigs were grown to have the weight of 30 kg. The breeding room was divided into a living section, a bed section, and a defecation section. The living section and the bed section may be positioned in the same compartment. However, a bed formed by stacking wood and sawdust was prepared to prevent a floor of a bed from getting wet. The defecation section was configured to have a separate compartment, and a part thereof was opened and closed as a passage for the pig so as to be convenient for daily management. This is based on the fact that pigs have the habit of having a constant place for defecation and urination. A reference area of the breeding room is 90 cm×90 cm for nurturing. Since pigs have a strong pushing force using a head, reinforcing bars are used as compartments for the pig room.

Breeding environmental conditions: Temperature and ventilation are important as environmental conditions. Pigs are resistant to a low temperature and vulnerable to a high temperature. However, since piglets have a thin subcutaneous fat and an immature body temperature control function, the low temperature conditions are required to be avoided. The temperature for piglets was adjusted at 25° C. to 34° C. during lactation, 24° C. after weaning, and 15° C. after 3 months ages or higher. An infrared lamp and an electric mat were used for warming. Humidity was maintained in the range of 50% to 65%, and a sufficient ventilation was provided to ensure the breathability.

Other management: It is important to keep a feed container and a water container clean above all. The water container was washed daily with water and regularly disinfected by a disinfectant combined with drinking water. To secure a feeding space sufficient for the piglet period is required for the feeding management. The amount of feed in the feeder was maintained at ⅓ or less, so that the loss of feed was reduced. Feed intake was stimulated by frequently operating the feeder.

2. Experimental Conditions on Experimental Group

The mini pigs were fed and managed under the same conditions as the control group, but only the feed mixture additives were differentiated. "Microalgae micro powder" as a feed additive was added to the feed of the experimental group. The microalgae micro powder of 100 g per 10 kg of blended feed was mixed and used.

3. Experimental Conditions on Control Group

The mini pig feeding management was performed without modification in the above common experimental conditions and compared with the experimental group.

Figure 15:
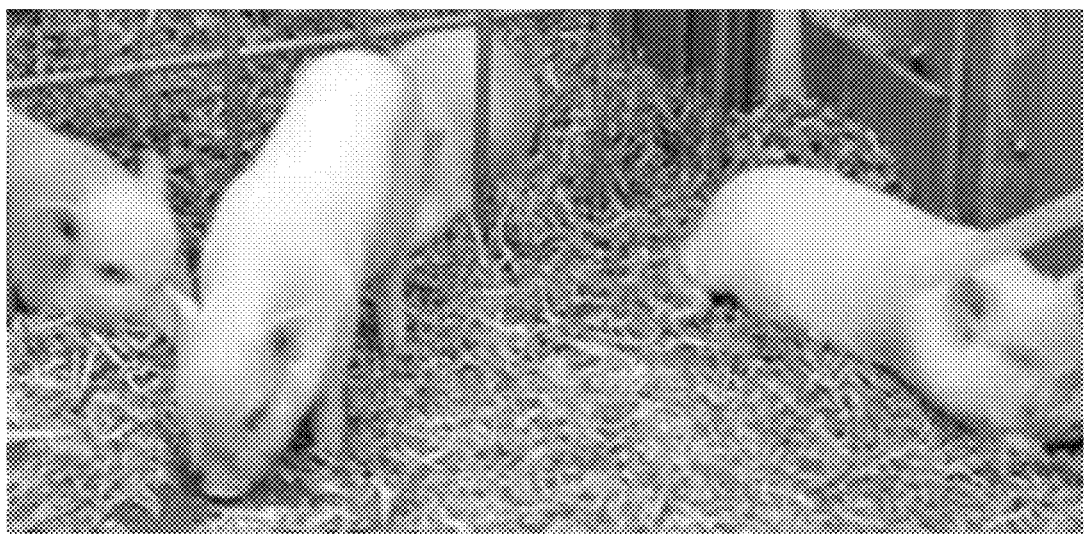
FIG. 15 is a diagram schematically showing an experiment process of a porcine production management to confirm the effectiveness of microalgae micro powder according to one embodiment of the present invention.
Figure 15:
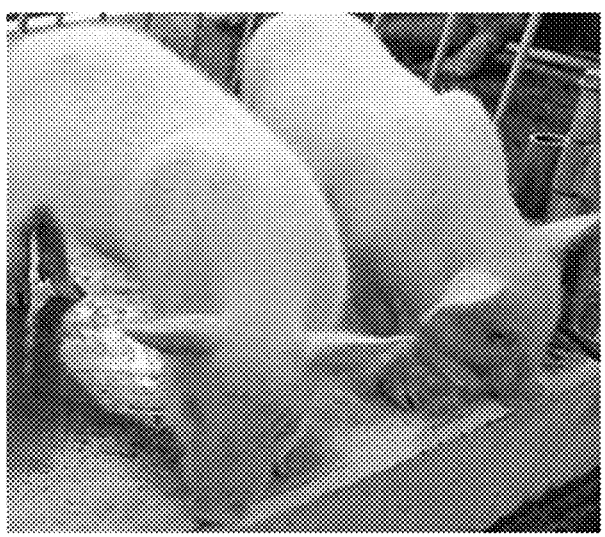
Figure 15:
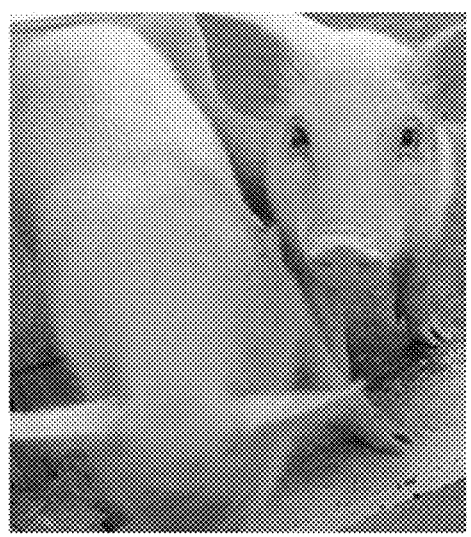

FIG. 15 is a diagram schematically showing an experiment process of a porcine production management to confirm the effectiveness of microalgae micro powder according to an embodiment of the present invention.

FIG. 15(a) shows 15-day-old subjects in the control group and the experimental group. FIG. 15(b) shows 200-day-old mini pig subjects being reared in a cage of the control group. FIG. 15(c) shows 200-day-old mini pig subjects being reared in a cage of the experimental group.

A diagnostic evaluation was performed on the 200-day-old mini pigs raised in the above manner. Table 13 summarizes the results of the performed evaluation as follows.

TABLE 13

| Item | Inspection items | Detailed criteria for inspection | Control group | Experimental group |
|---|---|---|---|---|
| Mouth | Lips | Whether having discoloration, redness, or lump | Normal | Normal |
| | | Whether having seizure | Normal | Normal |
| | | Whether the process of opening a mouth is normal | Normal | Normal |
| | Drooling | Whether drooling | Often and slightly | Normal |
| | Inner mouth | Whether having discoloration, redness, or lump of gums | Normal | Normal |
| | | Whether tongue is normal | Normal | Normal |
| | | Whether tonsils are normal | Normal | Normal |
| Chest (Respiratory, circulatory) | Respiration | Whether respiratory rate is normal | Sometimes breathlessness | Normal |
| | | Whether breathing with mouth open | Often open mouth | Normal |
| | | Whether coughing or sneezing | Sometimes | Normal |
| | | Whether having noise in breathing sounds | Normal | Normal |
| | Circulation in entire body | Whether oral mucosal color tone is normal | Normal | Normal |
| | | Capillary refill time | Normal | Normal |
| | | Whether moving amount is normal | Inactive | Active |
| | | Stability of pulse | Normal | Normal |
| | Structural integrity and symmetry | Symmetry of thorax | Normal | Normal |
| | | Whether having lump or edema | Normal | Normal |
| Abdomen (Digestive organs) | Structural integrity and symmetry | Whether having abdominal swelling | Normal | Normal |
| | | Whether having hernia | Normal | Normal |
| | Abdominal pain | Whether waist is bent | Normal | Normal |
| | | Whether having pain complaint upon | Normal | Normal |

TABLE 13-continued

| Item | Inspection items | Detailed criteria for inspection | Control group | Experimental group |
|---|---|---|---|---|
| | Digestive function | palpation Whether defecation is normal | Normal/Odor | Normal |
| Perineum (Urinary genitalia) | Anus | Cleanliness | Excreta remain/Odor | Normal |
| | | Phenomenon of dragging anus | Often | Normal |
| | Urination function | Whether urination is normal | Normal | Normal |
| | External genitalia | Whether structure is normal | Normal | Normal |
| | | Whether having secretion | Normal | Normal |
| Musculoskeletal system (including nervous system) | Structural integrity and symmetry | Whether limbs are normal | Normal | Normal |
| | | Whether toes move | Normal | Normal |
| | | Whether using limbs | Normal | Normal |
| | | Whether dragging leg | Normal | Normal |
| | | Whether muscle strength is normal | Slightly weak | Strong |
| | | Whether having limb pain complaint | Normal | Normal |
| Skin | Changes of skin | Presence of alopecia | Neck periphery | Normal |
| | | Whether having discoloration, redness, or lump | Redness around neck | Normal |
| | | Whether having clumped hairs | Around abdomen | Normal |
| | | Whether frequently losing hairs | Neck periphery | Normal |
| | | Whether itching | Neck periphery | Normal |

In addition, body compositions of grown mini pigs were analyzed and compared through feeding experiments.

Tables 14 and 15 summarize body compositions of the control group and the experimental group as follows. Each nutritional ingredient is indicated as a content per 100 g.

TABLE 14

Table on body composition analysis of control group

| Niacin | Natrium | Protein | Carbohydrate | Retinol |
|---|---|---|---|---|
| 5.70 mg | 58.00 mg | 21.10 g | 0.20 g | 5.00 μg |
| Beta-carotene | Vitamin A | Vitamin B1 | Vitamin B2 | Vitamin B6 |
| 0.00 μg | 5.00 μgRE | 0.56 mg | 0.16 mg | 0.57 mg |
| Vitamin C | Vitamin E | Dietary Fiber | Zinc | Folic acid |
| 2.00 mg | 0.29 mg | 0.00 g | 1.80 mg | 6.00 μg |
| Phosphorus | Lipid | Iron | Potassium | Calcium |
| 187.00 mg | 16.10 g | 1.60 mg | 304.00 mg | 7.00 mg |
| Omega-3 fatty acids | Omega-6 fatty acids | Cholesterol | | |
| 0.04% min | 2.71% min | 55.00 mg | | |

TABLE 15

Table on body composition analysis of experimental group

| Niacin | Natrium | Protein | Carbohydrate | Retinol |
|---|---|---|---|---|
| 8.11 mg | 60.03 mg | 20.70 g | 0.18 g | 6.42 μg |
| Beta-carotene | Vitamin A | Vitamin B1 | Vitamin B2 | Vitamin B6 |
| 0.00 μg | 15.12 μgRE | 3.20 μgRE | 1.15 mg | 1.00 mg |
| Vitamin C | Vitamin E | Dietary Fiber | Zinc | Folic acid |
| 4.75 mg | 3.14 mg | 0.00 g | 2.05 mg | 7.30 μg |
| Phosphorus | Lipid | Iron | Potassium | Calcium |
| 201.10 mg | 22.00 g | 2.05 mg | 380.52 mg | 35.71 mg |
| Omega-3 fatty acids | Omega-6 fatty acids | Cholesterol | Ge | Ash |
| 5.2% min | 0.8% min | 14.54 mg | 0.10 mg | 1.80 g |
| DHA | EPA | | | |
| 0.52 mg | 0.47 mg | | | |

Meanwhile, the mini pigs in the experimental group obtained through this experiment according to one embodiment of the present invention were monitored for the effectiveness as an SPF product. Table 10 summarizes the SPF monitoring test method for the mini pigs in the experimental group as follows.

TABLE 16

| Item | Pathogen | Inspection method (test method) |
|---|---|---|
| Virus | Hog cholera | ELISA test method |
| | Aujeszky (pseudorabies) | |
| | Porcine reproductive and respiratory syndrome virus (PRRS) | ELISA, RT-PCR test method |
| | Porcine circovirus type2 | ELISA test method |
| | Swine influenza (H1N1) | |
| Bacteria | Salmonella spp. | Bacterial Culture PCR test method |
| | Erysipelothrix rhusiopathiae | |
| | Bordetella spp. | |
| | Actinobacillus spp. | |
| | Mycoplasma hyopneumoniae | |

Table 17 summarizes the results of SPF monitoring the mini pigs in the experimental group as follows.

TABLE 17

| | |
|---|---|
| Hog cholera | ① Inspection method<br>Serum antibody ELISA inspection<br>ELISA kit<br>Protocol of manufacturer<br>② Inspection result<br>Number of samples: n = 2 (M001, M003)<br>All negative |
| Aujeszky (pseudorabies) | ① Inspection method<br>Serum antibody ELISA inspection<br>ELISA kit<br>Protocol of manufacturer<br>② Inspection result<br>Number of samples: n = 2 (M001, M003)<br>All negative |
| Porcine reproductive and respiratory syndrome virus (PRRS) | ① Inspection method<br>Serum antibody ELISA inspection<br>ELISA kit<br>Protocol of manufacturer<br>② Inspection result<br>Number of samples: n = 2 (M001, M003)<br>All negative<br>① Inspection method<br>PCR conditions<br>primer(firstround): sense: 5'-ATGGCCAGCCAGTCAATCA-3'<br>anti-sense: 5-TCGCCCTAATTGAATAGGTGA-3'<br>primer(second round): sense: 5'-CCAGTCAATCAGCTGTGCCA-3'<br>anti-sense: 5-CGGATCAGGCGCACAGTATG-3'<br>product size: First PCR 433 bp, second PCR 296 bp<br>condition<br>94° C. 2 min<br>94° C. 30 sec, 54° C. 30 sec, 68° C. 40 sec (32 cycle)<br>4° C. ∞<br>sample: whole blood<br>② Inspection result<br>Number of samples: n = 2 (M001, M003)<br>As a result of the inspection, PRRS virus was not detected in all samples. |
| Porcine circovirus type2 | ① Inspection method<br>Serum antibody ELISA inspection<br>ELISA kit<br>Protocol of manufacturer<br>② Inspection result<br>Number of samples: n = 2 (M001, M003)<br>All negative |
| Swine influenza (H1N1) | ① Inspection method<br>Serum antibody ELISA inspection<br>ELISA kit<br>Protocol of manufacturer<br>② Inspection result<br>Number of samples: n = 2 (M001, M003)<br>All negative |
| Salmonella spp. | ① Inspection method<br>XLD agar cultured after enriched in RV selective broth enrichment<br>② Inspection result<br>Number of samples: n = 2 (M001, M003)<br>Any colony presumed as salmonella was not confirmed in all samples |
| Erysipelothrix rhusiopathiae | ① Inspection method<br>PCR conditions<br>primer: sense: 5'-CGATTATATTCTTAGCACGCAACG-3'<br>anti-sense: 5-TGCTTGTGTTGTGATTTCTTGACG-3'<br>PCR product size: 937 bp<br>condition<br>94° C. 2 min<br>94° C. 30 sec, 54° C. 30 sec, 68° C. 40 sec (32 cycle)<br>4° C. ∞<br>sample: skin swab<br>② Inspection result<br>Number of samples: n = 2 (M001, M003)<br>As a result of the inspection, Erysipelothrix rhusiopathiae was not detected in all samples. |
| Bordetella spp. | ① Inspection method<br>PCR conditions<br>primer: sense: 5'-TGCCGCCTGCCCTATC3'<br>anti-sense: 5-AGGCYCCCAAGAGAGAAAGGCTT-3'<br>product size: 237 bp<br>condition<br>94° C. 2 min<br>94° C. 30 sec, 54° C. 30 sec, 68° C. 40 sec (32 cycle)<br>4° C. ∞<br>sample: nasal swab<br>② Inspection result<br>Number of samples: n = 2 (M001, M003)<br>As a result of the inspection, Bordetella spp. was not detected in all samples. |
| Actinobacillus spp. | ① Inspection method<br>PCR conditions<br>primer: sense: 5'-GGGCCGATGAAACCTATTAAAATAGCT-3'<br>anti-sense: 5-AGGCYCCCAAGAGAGAAAGGCTT-3'<br>product size: 422 bp<br>condition<br>94° C. 2 min<br>94° C. 30 sec, 54° C. 30 sec, 68° C. 40 sec (32 cycle)<br>4° C. ∞<br>sample: nasal swab<br>② Inspection result<br>Number of samples: n = 2 (M001, M003)<br>As a result of the inspection, Actinobacillus spp. was not detected in all samples. |
| Mycoplasma hyopneumoniae | ① Inspection method<br>PCR conditions<br>primer: sense: 5'-TGGCACTGACGGTGATGA-3'<br>anti-sense: 5-GGGGACCGACTCAACCAT-3'<br>product size: 948 bp<br>condition<br>94° C. 2 min<br>94° C. 30 sec, 54° C. 30 sec, 68° C. 40 sec (32 cycle)<br>4° C. ∞<br>sample: nasal swab<br>② Inspection result<br>Number of samples: n = 2 (M001, M003)<br>As a result of the inspection, Mycoplasma hyopneumoniae was not detected in all samples. |

As the results of various virus and bacteria monitoring tests on the mini pigs in the experimental group, any abnormality was not observed in all monitoring results.

According to an embodiment of the present invention, four kinds of functional microalgae of *Phaffia rhodozyma*, *Dunaliella salina, Chlorella vulgaris*, and *Spirulina Platensis* that are microalgae can be mass-produced so as to be processed into a dietary form for easy penetration performance.

According to an embodiment of the present invention, the culture efficiency, collecting efficiency, and food availability of the microalgae can be increased.

According to an embodiment of the present invention, the mutation of the microalgae may be induced so that the microalgae micro powder having increased contents of useful ingredients can be manufactured.

The descriptions of the described embodiments are provided to enable any person having ordinary skill in the art to use or execute the present invention. It shall be apparent to the person having ordinary skill in the art that various modifications are available for the embodiments, and general principles defined herein may be applied to other embodiments without departing from the scope of the present invention. Therefore, the present invention is not limited to the embodiments set forth herein, and should be construed in the broadest scope consistent with the principles and novel features set forth herein.

What is claimed is:

1. A method for manufacturing microalgae micro powder containing astaxanthin and useful fatty acids with penetration performance and food availability, the method comprising:
   (a) a microalgae culturing step of mass-culturing four microalgal strains, one of each of the following species—*Phaffia rhodozyma, Dunaliella salina, Chlorella vulgaris*, and *Spirulina platensis* in a medium;
   (b) a microalgae collecting step of separating and collecting the cultured microalgae from the medium;
   (c) an oil extracting step of extracting an oil ingredient by compressing the microalgae;
   (d) a powder processing step of pulverizing the oil-extracted microalgae; and
   (e) a powder mixing step of mixing the four microalgae powders of *Phaffia rhodozyma, Dunaliella salina, Chlorella vulgaris*, and *Spirulina platensis* that have been subjected to the powder processing step, wherein the microalgae culturing step, the microalgae collecting step, the oil extracting step, and the powder processing step are performed for each of the four microalgae.

2. The method of claim 1, wherein the powder mixing step includes mixing the powders of *Phaffia rhodozyma, Dunaliella salina, Chlorella vulgaris*, and *Spirulina platensis* in a ratio of equal amounts of each alga by weight.

3. The method of claim 1, wherein the microalgae culturing step for *Phaffia rhodozyma* includes:
   (a) a mutation promoting step of inducing a mutation by applying stress to a *Phaffia rhodozyma* culture;
   (b) a mutant selection step of selecting and separating a strain producing a higher amount of astaxanthin than the original *Phaffia rhodozyma* culture;
   (c) a medium composing step of composing a liquid medium for culturing *Phaffia rhodozyma*; and
   (d) a mass-culturing step of culturing the selected *Phaffia rhodozyma* strain in the liquid medium.

4. The method of claim 3, wherein the mutation promoting step includes adding methylnitronitrosoguanidine (MNNG) to the *Phaffia rhodozyma* culture to induce the mutation.

5. The method of claim 3, wherein the mutation promoting step includes inducing the mutation by performing the culture under a light condition with illuminance of 18,000 lx to 21,000 lx.

6. The method of claim 1, wherein the microalgae culturing step for *Dunaliella salina* includes:
   a) a mutation promoting step of inducing a mutation by applying stress to a *Dunaliella salina* culture;
   b) a mutant selecting step of selecting and separating a strain that produces a higher amount of beta-carotene than the original *Dunaliella salina* culture;
   c) a medium composing step of composing a liquid medium for culturing *Dunaliella salina*; and
   d) a mass-culturing step of culturing the selected *Dunaliella salina* in the liquid medium.

7. The method of claim 6, wherein the mutation promoting step includes inducing the mutation by performing the culture under a light condition with illuminance of 18,000 lx to 21,000 lx.

8. The method of claim 1, wherein the microalgae culturing step includes mass-culturing microalgae in a medium containing ionized calcium.

9. The method of claim 1, wherein the microalgae collecting step includes administering an aqueous ionized calcium solution having a content of 70 mg/L or more of calcium to culture water in which the microalgae are cultured; and collecting the microalgae floating on a surface of the solution.

* * * * *